United States Patent
Yang

(10) Patent No.: US 9,492,477 B2
(45) Date of Patent: Nov. 15, 2016

(54) COMPOSITIONS COMPRISING CITRATE AND APPLICATIONS THEREOF

(71) Applicant: The Board of Regents, The University of Texas System, Austin, TX (US)

(72) Inventor: Jian Yang, State College, PA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/146,272

(22) Filed: Jan. 2, 2014

(65) Prior Publication Data

US 2014/0193356 A1    Jul. 10, 2014

Related U.S. Application Data

(60) Provisional application No. 61/748,906, filed on Jan. 4, 2013.

(51) Int. Cl.

| | | |
|---|---|---|
| *C08G 63/91* | (2006.01) | |
| *A61K 31/785* | (2006.01) | |
| *A61K 31/765* | (2006.01) | |
| *C08G 63/12* | (2006.01) | |
| *C12N 5/077* | (2010.01) | |

(52) U.S. Cl.
CPC ........... *A61K 31/785* (2013.01); *A61K 31/765* (2013.01); *C08G 63/12* (2013.01); *C08G 63/914* (2013.01); *C12N 5/0669* (2013.01); *C12N 2500/34* (2013.01); *C12N 2501/155* (2013.01); *C12N 2533/18* (2013.01)

(58) Field of Classification Search
None
See application file for complete search history.

(56) References Cited

U.S. PATENT DOCUMENTS

| | | |
|---|---|---|
| 5,480,963 A | 1/1996 | Jiang et al. |
| 8,148,569 B1 | 4/2012 | O'Lenick et al. |
| 8,192,726 B1 | 6/2012 | O'Lenick et al. |
| 8,277,787 B1 | 10/2012 | O'Lenick et al. |
| 8,530,611 B2 | 9/2013 | Yang et al. |
| 8,574,311 B2 | 11/2013 | Yang et al. |
| 8,613,944 B2 | 12/2013 | Yang et al. |
| 2002/0082694 A1* | 6/2002 | McKay ................. 623/17.11 |
| 2003/0180344 A1 | 9/2003 | Wise et al. |
| 2003/0185752 A1 | 10/2003 | Nathan et al. |

(Continued)

FOREIGN PATENT DOCUMENTS

| | | |
|---|---|---|
| WO | WO-96/02276 A2 | 2/1996 |
| WO | WO-2011/130539 A2 | 10/2011 |

OTHER PUBLICATIONS

Qiu et al., Biomaterials, 2006, vol. 27, pp. 5845-5854.*

(Continued)

*Primary Examiner* — Brian Gulledge
(74) *Attorney, Agent, or Firm* — McCarter & English, LLP

(57) ABSTRACT

In one aspect, methods of promoting bone growth are described herein. In some embodiments, a method of promoting bone growth described herein comprises promoting cell differentiation or phenotype progression in a population of bone cells by providing a citrate-presenting composition to the population of bone cells. In some embodiments, the citrate-presenting composition is provided to the bone cells at a first stage of cell development selected to obtain a first cell differentiation or phenotype progression. Additionally, in some cases, a second citrate-presenting composition is further provided to the bone cells at a second stage of cell development selected to obtain a second cell differentiation or phenotype progression.

15 Claims, 17 Drawing Sheets

(56) References Cited

U.S. PATENT DOCUMENTS

| | | |
|---|---|---|
| 2003/0185871 A1 | 10/2003 | Nathan et al. |
| 2004/0120981 A1 | 6/2004 | Nathan |
| 2004/0122205 A1 | 6/2004 | Nathan |
| 2004/0253203 A1 | 12/2004 | Hossainy et al. |
| 2005/0063939 A1 | 3/2005 | Ameer et al. |
| 2007/0071790 A1 | 3/2007 | Ameer et al. |
| 2008/0086199 A1 | 4/2008 | Dave et al. |
| 2008/0262613 A1 | 10/2008 | Gogolewski |
| 2009/0093565 A1* | 4/2009 | Yang et al. .................... 523/113 |
| 2009/0148945 A1 | 6/2009 | Ameer et al. |
| 2009/0325859 A1 | 12/2009 | Ameer et al. |
| 2010/0036476 A1 | 2/2010 | Ameer et al. |
| 2010/0076162 A1 | 3/2010 | Ameer et al. |
| 2010/0145469 A1* | 6/2010 | Barralet .............. A61F 2/30767 623/23.56 |
| 2011/0008277 A1 | 1/2011 | Bruggeman et al. |
| 2011/0071079 A1 | 3/2011 | Ameer et al. |
| 2011/0124765 A1 | 5/2011 | Yang et al. |
| 2011/0142790 A1 | 6/2011 | Chen |
| 2011/0159113 A1 | 6/2011 | Adeli et al. |
| 2011/0183435 A1 | 7/2011 | Yang et al. |
| 2011/0280937 A1 | 11/2011 | Moriuchi et al. |
| 2012/0053303 A1 | 3/2012 | Djuric et al. |
| 2012/0136088 A1 | 5/2012 | Aizawa et al. |
| 2012/0225972 A1 | 9/2012 | Ameer et al. |
| 2012/0237443 A1 | 9/2012 | Ameer et al. |
| 2012/0238521 A1 | 9/2012 | Sun et al. |
| 2012/0244108 A1 | 9/2012 | Yang et al. |
| 2012/0322155 A1 | 12/2012 | Ameer et al. |

OTHER PUBLICATIONS

Qui, H., et al., "A citric acid-based hydroxyapatite composite for orthopedic implants", Biomaterials, Elsevier Science Publishers BV., Barking, GB, vol. 27, No. 34, Dec. 1, 2006, pp. 5845-5854.

Djordjevic, Ivan, et al., "Osteoblast Biocompatibility of Poly(octanediol citrate)/Sebacate Elastomers with Controlled Wettability", Journal of Biomaterials Science, Polymer Edition, VSP, Utrecht, NL, vol. 21, Nos. 8-9, Jan. 1, 2010, pp. 1039-1050.

Dey, J., et al., "Development of biodegradable crosslinked urethane-doped polyester elastomers", Biomaterials, Elsevier Science Publishers BV, Barking, GB, vol. 29, No. 35, Dec. 1, 2008, pp. 4637-4649.

Tran, Richard T., et al., "Synthesis and characterization of biomimetric citrate-based biodegradable composites", Journal of Biomedical Materials Research Part A, John Wiley & Sons, Aug. 1, 2013, pp. 1-12.

Yokoyama, A., et al., "Development of calcium phosphate cement using chitosan and citric acid for bone substitute materials", Biomaterials, Elsevier Science Publishers BV., Barking, GB, vol. 23, No. 4, Feb. 15, 2002, pp. 1091-1101.

Webb, Antonio R., et al., "Biodegradable polyester elastomers in tissue engineering", Expert Opinion on Biological Therapy, Ashley, London, GB, vol. 4, No. 6, Jun. 1, 2004, pp. 801-812.

International Search Report for copending PCT Application No. PCT/US2014/010057, mailed Apr. 4, 2014, 5 pages.

* cited by examiner

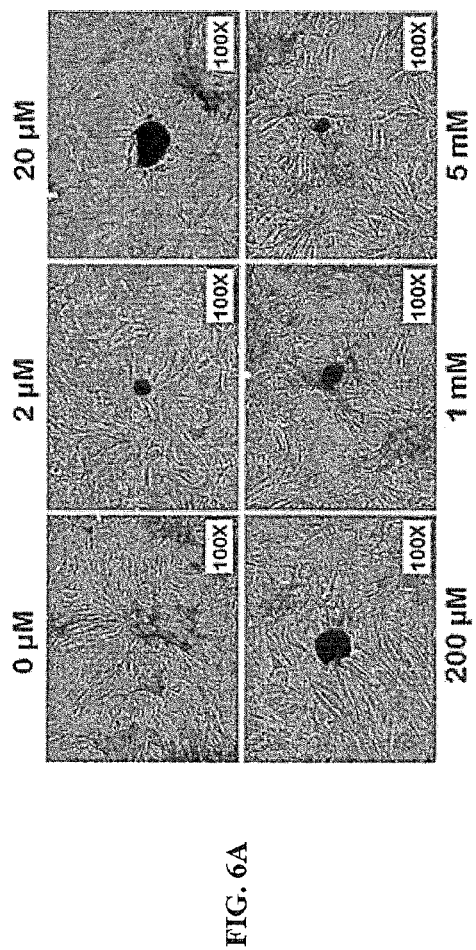
FIG. 6A
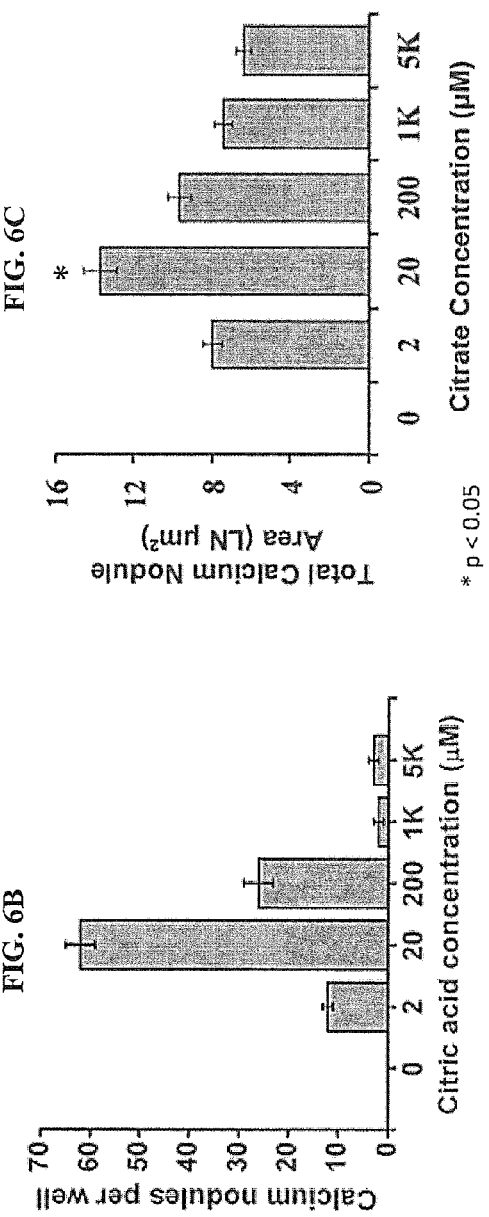
FIG. 6B
FIG. 6C

COMPOSITIONS COMPRISING CITRATE AND APPLICATIONS THEREOF

CROSS REFERENCE TO RELATED APPLICATION

This application claims priority pursuant to 35 U.S.C. §119(e) to U.S. Provisional Patent Application Ser. No. 61/748,906, filed on Jan. 4, 2013, which is hereby incorporated by reference in its entirety.

STATEMENT REGARDING FEDERALLY SPONSORED RESEARCH

This invention was made with government support under grant 0954109 awarded by the National Science Foundation (NSF) and grant EB012575 awarded by the National Institutes of Health (NIH). The government has certain rights in the invention.

FIELD

This invention relates to citrate-presenting compositions and, in particular, to citrate-presenting compositions for bone applications.

BACKGROUND

The native bone matrix is a composite comprising about 60 to 65% by weight of inorganic materials embedded within a collagen protein matrix. In addition, a thin layer of apatite nanocyrstals is embedded within the collagen network. Some engineered biomaterials have therefore combined various inorganic materials with synthetic polymers for use in bone tissue engineering applications. However, some existing biomaterials fail to match the native composition of bone, provide adequate mechanical support, minimize inflammatory responses, quickly promote bone regeneration, and/or fully integrate with surrounding tissue.

Therefore, there exists a need for compositions and methods that provide improved properties for various orthopedic and bone applications, including improved mechanical properties and/or improved bone growth properties.

SUMMARY

In one aspect, compositions are described herein which, in some cases, can provide one or more advantages compared to other compositions for bone applications. For example, in some embodiments, a composition described herein can provide improved mechanical properties, reduced inflammatory responses, improved biodegradability, and superior integration with surrounding tissue. Further, in some cases, a composition described herein can promote bone growth in an improved manner, including by promoting cell differentiation or phenotype progression in a population of bone cells such as a population comprising stem cells or osteoblast cells. In addition, in some instances, a composition described herein can also inhibit the growth of cancer, including bone cancer.

A composition described herein, in some embodiments, is a citrate-presenting composition. For example, in some cases, a citrate-presenting composition described herein comprises a polymer or oligomer comprising a citrate moiety. In some embodiments, a composition described herein comprises a first polymer or oligomer having the structure of Formula (I) described hereinbelow and a second polymer or oligomer having the structure of Formula (II) described hereinbelow, wherein the first polymer or oligomer is blended with the second polymer or oligomer. Further, in some cases, the first polymer or oligomer and the second polymer or oligomer are cross linked with one another to form a polymer network. Additionally, in some instances, the composition further comprises a particulate material dispersed in the polymer network. The particulate material can be one or more of hydroxyapatite, tricalcium phosphate, biphasic calcium phosphate, bioglass, ceramic, magnesium powder, magnesium alloy, and decellularized bone tissue particles.

Moreover, in some embodiments, a composition described herein further comprises bone tissue adhered to the polymer network. In some cases, the bone tissue surrounds the polymer network and the polymer network is integrated into the bone tissue.

In another aspect, methods of promoting bone growth are described herein which, in some instances, can provide one or more advantages over other methods. In some cases, for example, a method described herein promotes cell differentiation or phenotype progression in a population of bone cells, the method comprising providing a citrate-presenting composition to the bone cells. In some embodiments, the citrate-presenting composition is provided to the bone cells at a first stage of cell development selected to obtain a first cell differentiation or phenotype progression. Additionally, in some cases, a second citrate-presenting composition is further provided to the bone cells at a second stage of cell development selected to obtain a second cell differentiation or phenotype progression. Bone cells treated in accordance with a method described herein can be in vitro or in vivo. In some cases, the bone cells comprise bone stem cells. In addition, in some embodiments, a method of promoting bone growth described herein comprises disposing a citrate-presenting composition in a biological environment. Further, in some embodiments, promoting bone growth comprises up-regulating osterix (OSX) gene expression and/or alkaline phosphatase (ALP) gene expression in the biological environment. In some instances, promoting bone growth comprises improving osteoconductivity and/or osteoinductivity in the biological environment. In some embodiments, promoting bone growth comprises promoting mineralization or calcium deposit formation in the biological environment. Further, in some cases, a method described herein is also effective for at least partially inhibiting the growth and/or proliferation of cancer cells, including bone cancer cells. Moreover, in some embodiments, one or more of the foregoing effects are provided by a citrate-presenting composition in a dose-dependent manner.

A citrate-presenting composition provided to bone cells and/or disposed in a biological environment according to a method described herein can comprise any composition described hereinabove. For example, in some embodiments, the citrate-presenting composition comprises a polymer or oligomer comprising a citrate moiety, such as a polymer or oligomer having the structure of Formula (I) or Formula (II). Other polymers or oligomers may also be used. Moreover, in some such embodiments, a method described herein further comprises releasing citrate from the polymer or oligomer by degrading the polymer or oligomer. In other instances, the citrate-presenting composition comprises citric acid or aqueous citrate. In some embodiments, the citrate-presenting composition comprises culture medium supplemented with citric acid or citrate. Further, in some cases, a citrate-presenting composition used in a method described herein provides a citrate concentration between about 20 μM and about 2000 μM, based on the volume of the composition. Additionally, in some instances, a method described herein further comprises providing a biological factor such as BMP-2 to the bone cells.

In yet another aspect, articles comprising citrate-presenting compositions are described herein. In some embodiments, an article comprises a citrate-presenting composition described hereinabove, such as a cross linked polymer network formed from a polymer or oligomer having the structure of Formula (I) and/or a polymer or oligomer having the structure of Formula (II). Moreover, in some cases, an article described herein forms a biological or surgical implant such as an orthopedic fixation device such as a bone screw.

These and other embodiments are described in more detail in the detailed description which follows.

BRIEF DESCRIPTION OF THE FIGURES

FIG. 6A illustrates optical microscope images of calcium nodule formation according to some embodiments of methods described herein.

FIG. 6B illustrates calcium nodule formation data according to some embodiments of methods described herein.

FIG. 6C illustrates calcium nodule formation data according to some embodiments of methods described herein.

DETAILED DESCRIPTION

Figure 1:
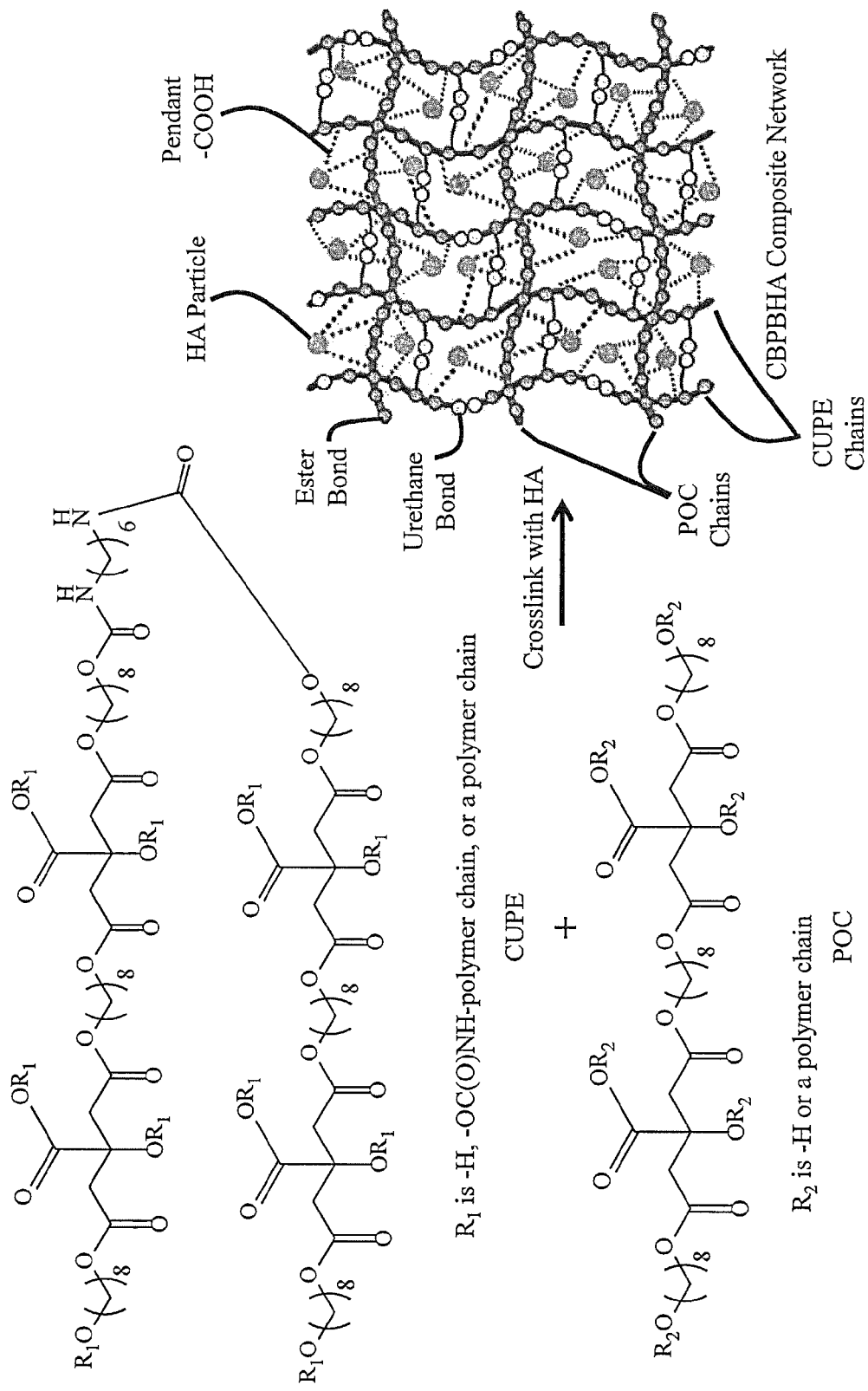
FIG. 1 illustrates a scheme for forming a composite network according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Compositions Comprising Citrate

In one aspect, compositions comprising citrate or presenting citrate are described herein. In some embodiments, a composition comprises a polymer or oligomer comprising a citrate moiety. A "citrate moiety," for reference purposes herein, comprises a moiety having the structure of Formula (III):

wherein $R_1$, $R_2$, and $R_3$ are independently —H, —CH$_3$, —CH$_2$CH$_3$, M$^+$, or a point of attachment to the remainder of the polymer or oligomer;

$R_4$ is —H or a point of attachment to the remainder of the polymer or oligomer; and M$^+$ is a cation such as Na$^+$ or K$^+$, provided that at least one of $R_1$, $R_2$, $R_3$, and $R_4$ is a point of attachment to the remainder of the polymer or oligomer.

Any polymer or oligomer not inconsistent with the objectives of the present invention may be used. For example, in some cases, a polymer or oligomer of a composition described herein comprises the reaction product of (i) citric acid, a citrate, or an ester of citric acid such as triethyl citrate with (ii) a polyol such as a diol. Non-limiting examples of polyols suitable for use in some embodiments described herein include C2-C20 α,ω-n-alkane diols or C2-C20 α,ω-alkene diols. In other instances, a polymer or oligomer of a composition described herein comprises the reaction product of (i) citric acid, a citrate, or an ester of citric acid with (ii) a polyol, and (iii) an amine, an amide, or an isocyanate. An amine, in some cases, comprises one or more primary amines having two to ten carbon atoms. In other cases, an amine comprises one or more secondary or tertiary amines having two to fifteen carbon atoms. An isocyanate, in some embodiments, comprises a monoisocyanate. In other instances, an isocyanate comprises a diisocyanate such as an alkane diisocyanate. In addition, a polymer or oligomer of a composition described herein can also comprise the reaction product of (i) citric acid, a citrate, or an ester of citric acid with (ii) a polyol, and (iii) a polycarboxylic acid such as a dicarboxylic acid or a functional equivalent of a polycarboxylic acid, such as a cyclic anhydride or an acid chloride of a polycarboxylic acid. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. In still other embodiments, a polymer or oligomer of a composition described herein comprises the reaction product of (i) citric acid, a citrate, or an ester of citric acid with (ii) a polyol, and (iii) an amino acid such as an alpha-amino acid. An alpha-amino acid, in some embodiments, comprises an L-amino acid, a D-amino acid, or a D,L-amino acid. In some cases, an alpha-amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 "standard" or proteinogenic amino acids, such as methyl serine. Additionally, in some cases, an amino acid forms a pendant group or side group of the polymer or oligomer of a composition described herein. Moreover, a reaction product of monomers described herein, in some cases, is a condensation reaction product of the monomers. In some cases, a polymer or oligomer of a composition described herein is a polymer or oligomer described in U.S. Pat. Nos. 8,530,611; 8,574,311; or No. 8,613,944.

In addition, in some embodiments, a polymer or oligomer of a composition described herein is formed from one or more monomers of Formula (A) and one or more monomers of Formula (B) or (B'):

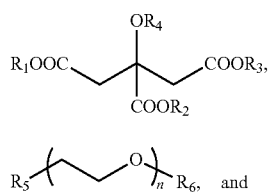

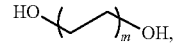

wherein $R_1$, $R_2$, and $R_3$ are independently —H, —CH$_3$, —CH$_2$CH$_3$, or M$^+$;
$R_4$ is —H;
$R_5$ is —H, —OH, —OCH$_3$, —OCH$_2$CH$_3$, —CH$_3$, or —CH$_2$CH$_3$;
$R_6$ is —H, —CH$_3$, or —CH$_2$CH$_3$;
M$^+$ is a cation such as Na$^+$ or K$^+$; and
n and m are independently integers ranging from 1 to 20.
In some cases, for instance, $R_1$, $R_2$, and $R_3$ are —H, $R_5$ is —OH, and $R_6$ is —H.

In some embodiments, a polymer or oligomer of a composition described herein is formed from one or more monomers of Formula (A), one or more monomers of Formula (B) or (B'), and one or more monomers of Formula (C):

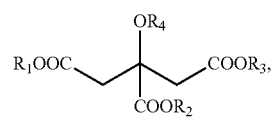

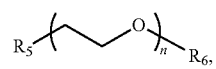

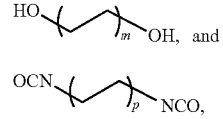

wherein $R_1$, $R_2$, and $R_3$ are independently —H, —CH$_3$, —CH$_2$CH$_3$, or M$^+$;
$R_4$ is —H;
$R_5$ is —H, —OH, —OCH$_3$, —OCH$_2$CH$_3$, —CH$_3$, or —CH$_2$CH$_3$;
$R_6$ is —H, —CH$_3$, or —CH$_2$CH$_3$;
M$^+$ is a cation such as Na$^+$ or K$^+$;
n and m are independently integers ranging from 1 to 20; and
p is an integer ranging from 1 to 10.
For example, in some instances, $R_1$, $R_2$, and $R_3$ are —H, or —CH$_2$CH$_3$, $R_5$ is —OH, $R_6$ is —H, n is 2 to 6, m is 2 to 8, and p is 2 to 6.

Further, in some embodiments of polymers or oligomers described herein, a monomer of Formula (B) or (B') can be replaced by an alcohol that does not have the formula of Formula (B) or (B'). For example, in some embodiments, an unsaturated alcohol or an unsaturated polyol can be used. Moreover, in some embodiments, a monomer or oligomer of Formula (C) can be at least partially replaced by an amino acid described herein.

Additionally, a polymer or oligomer of a composition described herein can have at least one ester bond in the backbone of the polymer or oligomer. In some cases, a polymer or oligomer has a plurality of ester bonds in the backbone of the polymer or oligomer, such as at least three ester bonds, at least four ester bonds, or at least five ester bonds. In some embodiments, a polymer or oligomer described herein has between two ester bonds and fifty ester bonds in the backbone of the polymer or oligomer.

A polymer or oligomer described herein can be present in a composition in any amount not inconsistent with the objectives of the present invention. In some embodiments, for instance, a composition described herein comprises up to about 99 weight percent, up to about 95 weight percent, up to about 90 weight percent, up to about 80 weight percent, up to about 70 weight percent, up to about 50 weight percent, up to about 40 weight percent, or up to about 30 weight percent polymer or oligomer. In some cases, a composition described herein comprises between about 20 and about 99 weight percent, between about 30 and about 95 weight percent, between about 30 and about 90 weight percent, between about 40 and about 90 weight percent, between about 40 and about 80 weight percent, between about 50 and about 95 weight percent, between about 50 and about 90 weight percent, between about 50 and about 80 weight percent, between about 50 and about 70 weight percent, between about 60 and about 99 weight percent, or between about 60 and about 80 weight percent.

Moreover, a composition described herein, in some cases, can comprise a mixture, blend, or combination of two or more polymers or oligomers. In some instances, the two or more polymers or oligomers are citrate-containing polymers or oligomers described herein. In other cases, at least one polymer or oligomer of the mixture, blend, or combination does not comprise a citrate moiety. For example, in some cases, a composition described herein comprises a mixture, blend, or combination of a citrate-containing polymer or oligomer described herein with a biodegradable polymer such as a polyester. In some embodiments, a composition described herein comprises a mixture, blend, or combination of a citrate-containing polymer or oligomer described herein with a poly(lactic acid), a poly(methylmethacrylate), a poly(methacrylate), a poly(acrylic acid), a poly(acrylate), a polycarbonate, a polysaccharide such as cellulose, or a combination thereof.

In some embodiments, a composition described herein comprises a first polymer or oligomer having the structure of Formula (I):

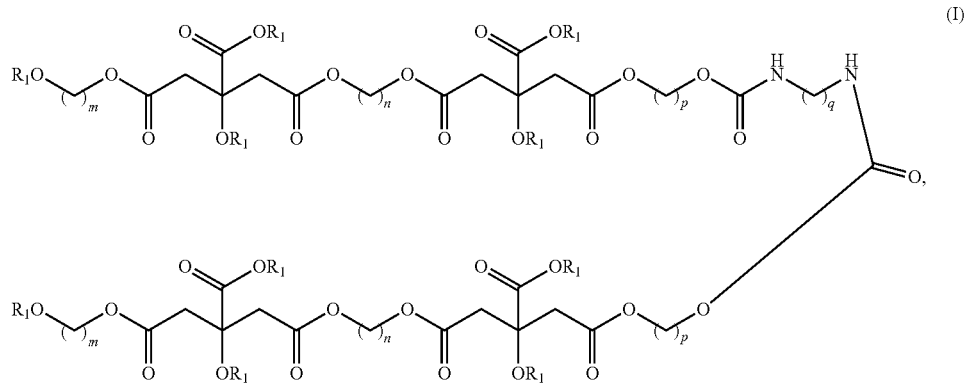

wherein $R_1$ is —H, —OC(O)NH〰〰, or 〰〰;

〰〰 represents an additional chain of repeating units having the structure of Formula (I); and m, n, p, and q are independently integers ranging from 2 to 20; and a second polymer or oligomer having the structure of Formula (II):

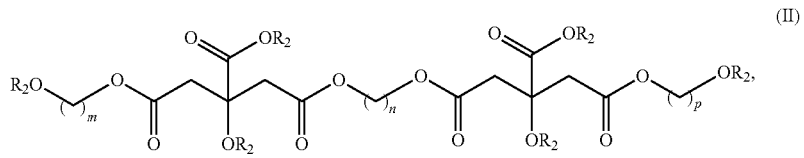

wherein $R_2$ is —H or 〰〰;

〰〰 represents an additional chain of repeating units having the structure of Formula (II); and m, n, and p are independently integers ranging from 2 to 20, and wherein the first polymer or oligomer is blended with the second polymer or oligomer.

The polymers or oligomers of a mixture, blend, or combination described herein can be present in the mixture, blend, or combination in any amount not inconsistent with the objectives of the present invention. In some cases, the weight ratio of a first polymer or oligomer of a mixture, blend, or combination of polymers or oligomers to a second polymer or oligomer of the mixture, blend, or combination is between about 99:1 and about 1:99. In some instances, the weight ratio of the first polymer or oligomer to the second polymer or oligomer is between about 10:1 and about 1:10, between about 5:1 and about 1:5, between about 3:1 and about 1:3, or between about 2:1 and about 1:2. Not intending to be bound by theory, it is believed that a composition comprising a mixture of polymers or oligomers described herein, in some embodiments, can be used to form a composite comprising higher amounts of particulate materials than otherwise possible. Again not intending to be bound by theory, it is further believed that a composition comprising a mixture of polymers or oligomers described herein can provide a desired combination of properties provided by the individual polymers or oligomers. For instance, a polymer or oligomer of Formula (I) may provide greater mechanical strength than a polymer or oligomer of Formula (II), but fewer hydroxyl or carboxyl groups for interacting with a particulate material such as hydroxyapatite. Thus, in some cases, the ratio of differing polymer or oligomers included in a composition described herein is selected based on a desired amount of one or more functional groups or moieties and/or a desired mechanical strength of the composition. For example, in some instances, a composition comprising a relatively large amount of a polymer or oligomer of Formula (II), compared to the amount of a polymer or oligomer of Formula (I), can have a higher amount of carboxyl groups than a composition comprising a relatively small amount of a polymer or oligomer of Formula (II).

Moreover, in some embodiments, the polymers or oligomers of a mixture, blend, or combination of polymers or oligomers described herein can be cross linked with one another to form a polymer network. Cross linking of a first polymer or oligomer with a second polymer or oligomer can be achieved in any manner not inconsistent with the objectives of the present invention. For example, in some cases, cross linking is achieved through intermolecular covalent bonds such as ester or amide bonds between polymers or oligomers, including by means of a condensation reaction. In other instances, cross linking can be achieved through the coupling of unsaturated moieties in the polymers or oligomers, such as ethyleneically unsaturated moieties of maleic acid moieties.

In addition, in some embodiments, a composition comprising a polymer network can further comprise a particulate material dispersed in the polymer network. Any particulate material not inconsistent with the objectives of the present invention may be used. In some cases, the particulate material comprises one or more of hydroxyapatite, tricalcium phosphate, biphasic calcium phosphate, bioglass, ceramic, magnesium powder, magnesium alloy, and decellularized bone tissue particles. Other particulate materials may also be used.

In addition, a particulate material described herein can have any particle size and/or particle shape not inconsistent with the objectives of the present invention. In some embodiments, for instance, a particulate material has an average particle size in at least one dimension of less than about 1000 µm, less than about 800 µm, less than about 500 µm, less than about 300 µm, less than about 100 µm, less than about 50 µm, less than about 30 µm or less than about 10 µm. In some cases, a particulate material has an average particle size in at least one dimension of less than about 1 µm, less than about 500 nm, less than about 300 nm, less than about 100 nm, less than about 50 nm, or less than about 30 nm. In some instances, a particulate material has an average particle size recited herein in two dimensions or three dimensions. Moreover, a particulate material can be formed of substantially spherical particles, plate-like particles, needle-like particles, or a combination thereof. Particulate materials having other shapes may also be used.

A particulate material can be present in a composition described herein in any amount not inconsistent with the objectives of the present invention. For example, in some cases, a composition comprises up to about 70 weight percent, up to about 60 weight percent, up to about 50 weight percent, up to about 40 weight percent, or up to about 30 weight percent particulate material, based on the total weight of the composition. In some instances, a composition comprises between about 1 and about 70 weight percent, between about 10 and about 70 weight percent, between about 15 and about 60 weight percent, between about 25 and about 65 weight percent, between about 25 and about 50 weight percent, between about 30 and about 70 weight percent, between about 30 and about 50 weight percent, between about 40 and about 70 weight percent, or between about 50 and about 70 weight percent, based on the total weight of the composition. For example, in some cases, a composition comprising a polymer network described herein comprises up to about 65 weight percent hydroxyapatite. Not intending to be bound by theory, it is believed that the incorporation of up to about 65 weight percent hydroxyapatite in a polymer network described herein can enhance the osteoconductivity and/or osteointegration provided by the polymer network in a biological environment or in vitro.

Further, a particulate material described herein can be dispersed in a polymer network in any manner not inconsistent with the objectives of the present invention. In some embodiments, for instance, the particulate material is mixed or ground into the polymer network. In addition, a particulate material described herein, in some cases, can be chelated or otherwise bound by one or more pendant functional groups of the polymer network. For instance, in some cases, a composition comprises hydroxyapatite particles dispersed in a polymer network described herein, wherein the hydroxyapatite is chelated by one or more pendant functional groups of the polymer network. In some embodiments, one or more carboxyl moieties or one or more citrate moieties of the polymer network chelate one or more calcium-containing portions of the hydroxyapatite. Not intending to be bound by theory, it is believed that such chelation can permit the incorporation of larger amounts of hydroxyapatite (or another inorganic material) within a polymer network described herein, compared to some other polymer matrices.

A polymer or oligomer or cross linked polymer network of a composition described herein, in some embodiments, can exhibit one or more desirable properties for biomedical or tissue engineering applications. For example, in some cases, a polymer or oligomer or a cross linked polymer network of a composition described herein is biodegradable. A "biodegradable" polymer or oligomer or cross linked polymer network, for reference purposes herein, degrades in vivo to non-toxic components which can be cleared from the body by ordinary biological processes. In some embodiments, a biodegradable polymer or oligomer or cross linked polymer network described herein completely or substantially completely degrades in vivo over the course of about 4 weeks or less. Further, in some embodiments, a polymer or oligomer or cross linked polymer network described herein is biocompatible or cytocompatible. A "biocompatible or cytocompatible" polymer or oligomer or cross linked polymer network, for reference purposes herein, is non-toxic and does not cause substantial tissue inflammation, where inflammation can be measured by the amount of fibrocapsule formation.

In addition, in some embodiments, a polymer or oligomer or cross linked polymer network of a composition described herein exhibits high mechanical strength. In some cases, for instance, a polymer or oligomer or cross linked polymer network of a composition described herein exhibits one or more properties described in Table I below, when measured as described hereinbelow in Example 2.

TABLE I

| Mechanical Properties. | | |
|---|---|---|
| Compressive Modulus (MPa) | Peak Load (N) | Peak Stress (MPa) |
| >2000 | >2000 | >70 |
| >2300 | >2300 | >90 |
| >3000 | >2500 | >100 |
| 1500-4000 | 1500-4000 | 70-130 |
| 1800-3800 | 2000-3500 | 70-120 |
| 2300-3600 | 2300-3300 | 85-120 |
| 2500-3500 | 2500-3100 | 90-120 |

Moreover, in some embodiments, a composition described herein can further comprise bone tissue. Any bone tissue not inconsistent with the objectives of the present invention may be used. In some embodiments, for instance, the bone tissue comprises compact bone tissue. In other cases, the bone tissue comprises spongy bone tissue. Further, in some embodiments, the bone tissue is adhered to a polymer network of the composition, including a polymer network described herein. Additionally, in some instances, the bone tissue surrounds the polymer network and the polymer network is integrated into the bone tissue. Such a composition, in some cases, can exhibit a high bone-to-implant contact (BIC), where the "bone" refers to the bone tissue and the "implant" refers to the polymer network. In some embodiments, a composition described herein exhibits a bone-to-implant contact of at least about 70 percent, at least about 80 percent, at least about 90 percent, at least about 95 percent, or at least about 99 percent, when measured as described herein. In some embodiments, a composition described herein exhibits a bone-to-implant contact between about 70 and about 99 percent, between about 75 and about 95 percent, between about 80 and about 95 percent, or between about 80 and about 90 percent, when measured as described herein. Further, in some cases, a composition described herein exhibits no fibrous tissue encapsulation or substantially no fibrous tissue encapsulation after six weeks in vivo. "Substantially no fibrous tissue encapsulation," for reference purposes herein, means that less than about 5 weight percent or less than about 1 weight percent of the composition encapsulates fibrous tissue.

It is to be understood that a composition described herein can have any combination of properties or features described herein not inconsistent with the objectives of the present invention. For example, any polymer or oligomer described herein can be used in combination with any amount or type of particulate material described herein. In some embodiments, for instance, a composition can comprise a polymer or oligomer having the structure of Formula (I) and/or Formula (II), wherein the one or more polymers or oligomers are cross linked to form a polymer network and a particulate material comprising hydroxyapatite is dispersed within the polymer network. Other combinations are also possible.

II. Methods of Promoting Bone Growth

In another aspect, methods of promoting bone growth are described herein. In some embodiments, a method of promoting bone growth comprises providing a citrate-presenting composition to a population of bone cells. Further, in some cases, promoting bone growth comprises promoting cell differentiation and/or phenotype progression in the population of bone cells. For example, in some instances, providing a citrate-presenting composition to a population of bone cells promotes osteoblast phenotype progression in the population of bone cells. Further, in some such embodiments, the citrate-presenting composition is provided to the bone cells at a first stage of cell development selected to obtain a first cell differentiation or phenotype progression. Additionally, in some cases, a second citrate-presenting composition can be further provided to the bone cells at a second stage of cell development selected to obtain a second cell differentiation or phenotype progression. In other embodiments, a method of promoting bone growth described herein comprises disposing a citrate-presenting composition in a biological environment. A "biological environment," for reference purposes herein, comprises an environment within a living organism, such as a bone site or a wound or injury site. In some cases, promoting bone growth comprises up-regulating osterix gene expression and/or alkaline phosphatase gene expression in the biological environment. Additionally, a method of promoting bone growth described herein, in some embodiments, further comprises releasing free citric acid or citrate from the citrate-presenting composition.

Turning now to steps of methods, methods of promoting bone growth described herein comprise providing a citrate-presenting composition to a population of bone cells and/or disposing a citrate-presenting composition in a biological environment. A "citrate-presenting composition," for reference purposes herein, is a composition that includes citric acid, a citrate, an ester of citric acid such as triethyl citrate, or a chemical species comprising a moiety having the structure of Formula (IV):

(IV)

wherein $R_1$, $R_2$, and $R_3$ are independently —H, —CH$_3$, —CH$_2$CH$_3$, M$^+$, or a point of attachment to the remainder of the chemical species;

$R_4$ is —H or a point of attachment to the remainder of the chemical species; and M$^+$ is a cation such as Na$^+$ or K$^+$. In some embodiments, the chemical species is a polymer or oligomer. Thus, the "citrate" of a "citrate-presenting composition" described herein can refer to a small molecule or "monomeric" form of citric acid, such as citric acid, a citrate salt, or an ester of citric acid, as described hereinabove.

Any citrate-presenting composition not inconsistent with the objectives of the present invention may be used in a method described herein. In some embodiments, for instance, a citrate-presenting composition comprises an aqueous solution of citric acid and/or a citrate such as sodium citrate or potassium citrate. In other cases, a citrate-presenting composition comprises a polymer or oligomer described hereinabove in Section I or a mixture, blend, or combination of polymers or oligomers described hereinabove in Section I. For example, in some embodiments, a citrate-presenting composition comprises a polymer or oligomer comprising a citrate moiety, such as a polymer or oligomer having the structure of Formula (I) or Formula (II). A citrate-presenting composition of a method described herein can also comprise a mixture, blend, or combination of a polymer or oligomer having the structure of Formula (I) and a polymer or oligomer having the structure of Formula (II). Other polymers or oligomers may also be used, as described hereinabove.

Further, a citrate-presenting composition described herein can be provided to a population of bone cells in any manner not inconsistent with the objectives of the present invention. For example, in some cases, a citrate-presenting composition is provided to the bone cells in vitro as an aqueous mixture or solution, including a culture medium supplemented with citrate. Any culture medium not inconsistent with the objectives of the present invention may be used. In some embodiments, for instance, the culture medium comprises Minimum Essential Medium Alpha (αMEM), Eagle's minimal essential medium (EMEM), Dulbecco's modified Eagle's medium, fetal bovine serum (FBS), or a mixture of one or more of the foregoing media. Moreover, in some cases wherein the citrate-presenting composition comprises a culture medium supplemented with citrate, the culture medium is free or substantially free of additional bone growth factors other than the citrate provided by a citrate-presenting composition described herein. In some embodiments, the culture medium is free or substantially free of zinc. A culture medium that is "substantially free" of additional bone growth factors or other components, for reference purposes herein, comprises less than about 10 µM or less than about 1 µM of additional bone growth factor. Alternatively, in other cases, a culture medium of a citrate-presenting composition described herein further comprises one or more bone growth factors. For example, in some cases, a culture medium is an osteogenic medium. In other instances, a citrate-presenting composition is provided to the bone cells in vivo as an aqueous mixture or solution or as a solid implant or device, such as a bone screw or bone plate. Further, it is to be understood that a citrate-presenting composition provided to bone cells according to a method described herein, in some embodiments, can be exogenous to the bone cells.

In addition, in some methods described herein, one or more citrate-presenting compositions can be provided to bone cells at one or more stages of phenotype progression or cell differentiation. Citrate-presenting compositions described herein can be provided to bone cells at any stage or combination of stages not inconsistent with the objectives of the present invention. In some cases, for instance, a citrate-presenting composition is provided to bone cells at or before a mineralization stage, including after the bone cells have at least partially differentiated. Citrate-presenting compositions may also be provided to bone cells at one or more other stages of phenotype progression or differentiation. In addition, the same or a different citrate-presenting composition described herein can be provided at one or more stages.

A method of promoting bone growth described herein, in some embodiments, further comprises releasing free citric acid or citrate from the citrate-presenting composition. "Free" citric acid or citrate, for reference purposes herein, comprises citric acid or citrate that is nto covalently bound to another species such as a polymer or oligomer described herein. Citric acid or citrate can be released from a citrate-presenting composition described herein in any manner not inconsistent with the objectives of the present invention. Additionally, the citric acid or citrate can be released into any desired environment. For example, in some cases, citric acid or citrate can be released into a biological environment by degrading a citrate-containing polymer or oligomer disposed in the biological environment. Moreover, a polymer or oligomer can be degraded in any manner not inconsistent with the objectives of the present invention. In some embodiments, degrading a polymer or oligomer comprises hydrolyzing an ester bond of the polymer or oligomer, such as an ester bond in the backbone of the polymer or oligomer.

In other cases, releasing citric acid or citrate from a citrate-presenting composition does not require hydrolysis, cleavage of chemical bonds, or other degradation of the composition. For example, in some embodiments comprising the use of aqueous solutions of citric acid or a citrate, free citric acid or citrate can be released into a desired environment simply by providing the citrate-presenting composition to the environment.

In addition, a citrate-presenting composition of a method described herein, in some instances, can provide a desired amount of citrate. In some embodiments, for instance, a citrate-presenting composition described herein provides a citrate concentration between about 20 µM and about 2000 µM, based on the volume of the composition. Surprisingly, it has been discovered that providing an amount of citrate between about 20 µM and about 2000 µM can promote bone growth in a manner described herein while also avoiding or minimizing other effects that may not be desired, as described further hereinbelow. Other amounts or concentrations of citrate can also be provided. For example, in some cases, a citrate-presenting composition described herein provides a citrate concentration between about 20 µM and about 200 µM, between about 20 µM and about 150 µM, between about 100 µM and about 2000 µM, between about 100 µM and about 1500 µM, between about 200 µM and about 2000 µM, between about 200 µM and about 1500 µM, between about 300 µM and about 1800 µM, between about 500 µM and about 2000 µM, between about 500 µM and about 1500 µM, between about 800 µM and about 2000 µM, between about 800 µM and about 1400 µM, between about 1000 µM and about 2000 µM, or between about 1000 µM and about 1500 µM. In some embodiments, a citrate-presenting composition described herein provides a citrate concentration greater than about 800 µM or greater than about 2000 µM.

Moreover, in some embodiments, a method described herein provides a biological effect in a dose-dependent manner, based on the amount of citrate provided. For example, in some cases, a method described herein comprises providing a citrate-presenting composition to a population of bone cells to up-regulate ALP and/or OSX gene expression in the cells in a dose-dependent manner, wherein the amount of citrate provided is between about 20 µM and about 2000 µM.

Further, a citrate-presenting composition described herein can be provided to any population of bone cells not inconsistent with the objectives of the present invention. For example, in some cases, the bone cells comprise osteoblast cells. In other cases, the bone cells comprise bone marrow cells such as bone marrow stromal cells. In some embodiments, the bone cells comprise stem cells. The stem cells, in some cases, can be adult stem cells. In some instances, the population of bone cells comprises multipotent, oligopotent, or unipotent stem cells. In some embodiments, the stell cells comprise mesenchymal stem cells such as C2C12 cells or human mesenchymal stem cells (hMSC). Moreover, the bone cells can be in vitro, in vivo, endogenous, or exogenous.

Methods of promoting bone growth described herein, in some embodiments, further comprise providing a biological factor to a population of bone cells. A "biological factor," for reference purposes herein, comprises a substance that functions in a specific biochemical pathway or bodily process, such as a growth factor. Any biological factor not inconsistent with the objectives of the present invention may be used. For example, in some embodiments, a biological factor comprises a bone morphogenetic protein (BMP). A BMP, in some cases, comprises one or more of BMP-2, BMP-3, BMP-4, BMP-6, and BMP-7. Other biological factors may also be used.

Methods of promoting bone growth described herein, in some embodiments, comprise up-regulating osterix (OSX) gene expression and/or alkaline phosphatase (ALP) gene expression. In some instances, up-regulating OSX gene expression comprises increasing the gene expression by up to about 300 percent compared to a bare glass control after 48 hours of culture. In some cases, the amount of OSX gene expression is increased by up to about 200 percent, up to about 100 percent, up to about 50 percent, or up to about 40 percent. In some embodiments, the amount of OSX gene expression is increased between about 30 percent and about 300 percent, between about 35 percent and about 250 percent, between about 35 percent and about 200 percent, or between about 200 percent and about 300 percent, compared to a bare glass control after 48 hours of culture.

In some instances, the amount of ALP gene expression is increased by an amount up to about 400 percent compared to a bare glass control after 48 hours of culture. In some cases, the amount of ALP gene expression is increased by up to about 360 percent, up to about 250 percent, up to about 150 percent, up to about 100 percent, up to about 50 percent, or up to about 40 percent. In some embodiments, the amount of ALP gene expression is increased between about 30 percent and about 400 percent, between about 35 percent and about 360 percent, between about 35 percent and about 300 percent, between about 35 percent and about 250 percent, between about 300 percent and about 400 percent, or between about 300 percent and about 360 percent, compared to a bare glass control after 48 hours of culture.

Additionally, methods described herein, in some embodiments, comprise providing a citrate-presenting composition that at least partially inhibits the growth and/or proliferation of cancer cells, such as osteosarcoma cells or other bone cancer cells. In some embodiments, the growth and/or proliferation of cancer cells is completely inhibited or arrested, such as when the cancer cells are killed by the method. In other instances, the growth and/or proliferation of cancer cells is inhibited by up to about 90 percent, up to about 80 percent, up to about 70 percent, up to about 50 percent, up to about 30 percent, or up to about 20 percent, compared to a control method that does not include providing a citrate-presenting composition to the population of cells. Moreover, in some embodiments, the effect of a citrate-presenting composition described herein is dose-dependent. Further, in some cases, inhibiting the growth and/or proliferation of cancer cells comprises providing citrate to the cells at a concentration greater than about 800 µM, such as an amount between about 800 µM and about 20,000 µM or an amount between about 800 µM and about 2000 µM.

Moreover, in some embodiments, methods described herein comprise providing a citrate-presenting composition that kills cancer cells such as bone cancer cells. In some cases, all of the cancer cells are killed. In other instances, at least about 90 percent, at least about 80 percent, at least about 70 percent, or at least about 50 percent of the cancer cells are killed, compared to a control method that does not include providing a citrate-presenting composition to the population of cells. Additionally, in some embodiments, the anti-cancer effect of a citrate-presenting composition described herein is dose-dependent. Further, in some cases, killing cancer cells comprises providing citrate to the cells at a concentration greater than about 2000 µM, such as a concentration greater than about 2000 µM and up to about 20,000 µM.

It is to be understood that a method of promoting bone growth described herein can comprise any combination of steps or use any combination of compositions described herein not inconsistent with the objectives of the present invention. In some embodiments, for instance, a method of promoting bone growth described herein can comprise using a citrate-presenting composition described hereinabove in Section I to provide a citrate concentration described hereinabove to a population of bone cells or to a biological environment described hereinabove for the purpose of promoting cell differentiation and/or phenotype progression or for the purpose of up-regulating osterix gene expression and/or alkaline phosphatase gene expression.

III. Articles Comprising Citrate-Presenting Compositions

In another aspect, articles comprising citrate-presenting compositions are described herein. In some embodiments, an article comprises or is formed from a citrate-presenting composition described hereinabove in Section I, such as a cross linked polymer network formed from a polymer or oligomer having the structure of Formula (I) and/or a polymer or oligomer having the structure of Formula (II). In some embodiments, an article described herein comprises or is formed from a cross linked polymer network described hereinabove in Section I comprising a particulate material dispersed in the polymer network. For example, in some cases, an article described herein comprises or is formed from a first polymer or oligomer having the structure of Formula (I) cross linked with a polymer or oligomer having the structure of Formula (II) to form a polymer network, the polymer network further comprising up to about 70 weight percent hydroxyapatite dispersed throughout the polymer network.

In some embodiments, an article described herein is a biological or surgical implant such as an orthopedic fixation device such as a bone screw or bone plate. Therefore, in some cases, an article described herein can be used to promote the healing or mending of bone fractures or other wounds or injuries by providing mechanical support. Moreover, in some embodiments, an article described herein can also promote bone growth at the site of a wound or injury such as a bone fracture. In this manner, an article described herein can be used to provide improved treatment of bone fractures, bone growth disorders, and/or bone degeneration conditions. An article described herein can also inhibit cancer growth or kill cancer cells in a biological compartment, such as bone.

An article described herein can have any size and shape not inconsistent with the objectives of the present invention. In some embodiments, an article described herein has a cylindrical shape, a spherical shape, or a polyhedral shape. In other instances, an article described herein has a shape suitable for use as an orthopedic fixation device, such as a screw shape or a plate shape.

Further, an article described herein can exhibit one or more desirable properties, such as one or more desirable biomedical or mechanical properties. In some instances, for example, an article described herein exhibits or promotes a biological effect described hereinabove in Section I or Section II, such as an increased gene expression effect or an osteoinductive effect. In other cases, an article described herein exhibits a compressive modulus described hereinabove in Section I.

In addition, an article described herein can be made in any manner not inconsistent with the objectives of the present invention. For example, in some cases, an article described herein is made from a composition described herein using an extrusion process, a pultrusion process, or a molding process, including but not limited to an injection molding process.

Some embodiments described herein are further illustrated in the following non-limiting examples. Unless otherwise noted, all experiments described below were conducted in duplicate and repeated three times (n=6), and statistical results are based on sets of three experiments. Where appropriate, data is expressed as the mean±one standard deviation. The statistical significance between two sets of data was calculated using a two-tail Student's t-test. Differences were taken to be significant when a value of P<0.05 was obtained.

EXAMPLE 1

POC and CUPE Polymers or Oligomers

Citrate-presenting polymers or oligomers according to some embodiments described herein were prepared as follows. A first polymer or oligomer was identified as poly (octanediol citrate) (POC), and a second polymer or oligomer was identified as cross linked urethane-doped polyester (CUPE).

To synthesize POC, equimolar amounts of 1,8-octanediol (98%, Sigma-Aldrich, St. Louis, Mo., USA) and citric acid (99.5%, Sigma-Aldrich, St. Louis, Mo., USA) were added to a 100 mL round bottom flask and exposed to a constant flow of nitrogen gas. The mixture was melted under vigorous stirring at 160-165° C. Once the constituents melted, the mixture was allowed to react at 140° C. for 1 h to create an unpurified POC polymer or oligomer. Next, the unpurified polymer or oligomer was added dropwise to deionized water, collected, and lyophilized overnight to obtain the purified POC polymer or oligomer.

To synthesize CUPE, a POC polymer or oligomer was first synthesized by reacting citric acid and 1,8-octanediol in a 1:1.1 molar ratio, respectively, and further processing the reaction product as stated above. Next, chain extension of the POC polymer or oligomer was accomplished by dissolving the purified POC polymer or oligomer in 1,4-dioxane to form a 3 weight percent solution of POC, followed by reaction with 1,6-hexamethyl diisocyanate (HDI) (Sigma-Aldrich, St. Louis, Mo., USA) in a 1:1.5 POC to HDI molar ratio under constant stirring at 55° C. The reaction was terminated when Fourier transform infrared (FT-IR) analysis showed a disappearance of the isocyanate peak at 2267 cm$^{-1}$.

EXAMPLE 2

CBPB Blends and CBPBHA Composites

Polymer networks and polymer networks comprising particulate material dispersed within the network according to some embodiments described herein were prepared as follows. The polymer networks included various blends of a first polymer or oligomer and a second polymer or oligomer and were designated as citrate-based polymer blends (CB-PBs). The polymer networks comprising particulate material were designated as citrate-based polymer blend/hydroxyapatite (CBPBHA) composites. CBPBHA composites were fabricated in three steps. First, a mixture of CUPE and POC was first prepared by dissolving a POC polymer or oligomer in 1,4-dioxane or tetrahydrofuran (THF) and mixing the POC solution with various weight ratios of solutions of CUPE polymer or oligomer in 1,4-dioxane or THF to form a homogenous citrate-based polymer or oligomer blend, designated as CBPB-X, where X is defined as the weight ratio of CUPE in the CBPB blend. Second, each CBPB was mixed with 65 weight percent hydroxyapatite (HA, [MW: 502.32; assay: >90% (as $Ca_3(PO_4)_2$); particle size: >75 μm (0.5%), 45-75 μm (1.4%), <45 μm (98.1%)], Fluka, St. Louis, Mo., USA), based on the total weight of the composition, and stirred in Teflon dishes pre-warmed to 50° C. to aid in solvent evaporation. Following solvent evaporation, the clay-like mixture was inserted into machined cylindrical metal molds and compressed into rod shaped samples. Finally, the resulting cylindrical composites were post-polymerized at 80° C. for 5 days followed by heating at 120° C. under 2 Pa vacuum for 1 day to form a crosslinked CBPBHA-X composite, where X is again defined as the weight ratio of CUPE in CBPB. The results are shown in Table II. Composites including particulate materials other than HA could also be prepared in the same manner. This process is illustrated schematically in FIG. 1. As depicted in FIG. 1, CUPE polymer or oligomer backbones are represented as being disposed essentially vertically, and POC polymer or oligomer backbones are represented as being disposed essentially horizontally. However, this depiction is for illustration purposes only. As understood by one of ordinary skill in the art, the orientation of the CUPE and POC backbones can be random. In addition, as depicted in FIG. 1, the larger circles in the composite network represent HA particles, the smaller circles represent ester or urethane linkages, and the dashed lines indicate pendant carboxyl groups.

TABLE II

CBPB Polymer Blends and CBPBHA Composites.

| Composition | CUPE (wt. %) | POC (wt. %) | HA (wt. %) |
|---|---|---|---|
| CBPB-100 | 100 | 0 | 0 |
| CBPB-90 | 90 | 10 | 0 |
| CBPB-50 | 50 | 50 | 0 |
| CBPB-0 | 0 | 100 | 0 |
| CBPBHA-100 | 100 | 0 | 65 |
| CBPBHA-90 | 90 | 10 | 65 |
| CBPBHA-80 | 80 | 20 | 65 |
| CBPBHA-70 | 70 | 30 | 65 |
| CBPBHA-60 | 60 | 40 | 65 |
| CBPBHA-50 | 50 | 50 | 65 |
| CBPBHA-0 | 0 | 100 | 65 |

Figure 2:
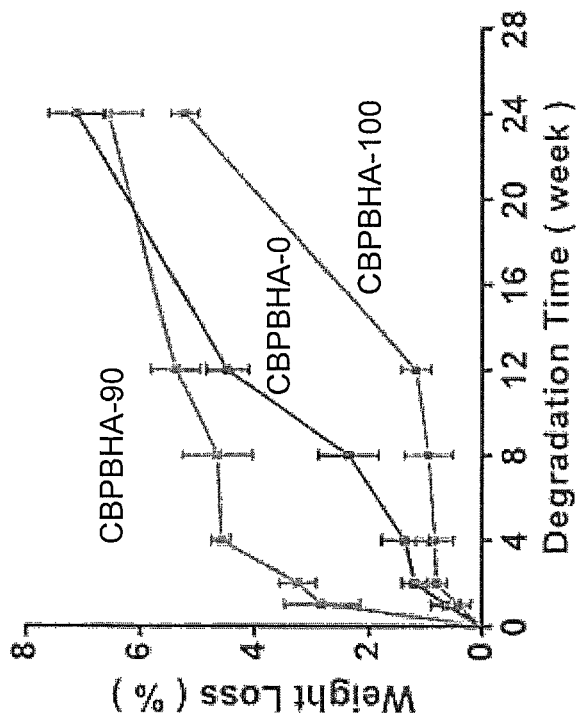
FIG. 2 illustrates a series of differential scanning calorimetry (DSC) thermograms for a series of compositions according to some embodiments described herein.

CBPB blends and CBPBHA composites were characterized using differential scanning calorimetry (DSC). Specifically, measurements were carried out using a DSC Q2000 Differential Scanning Calorimeter (TA Instruments, New Castle, Del., USA) to characterize the thermal properties and homogeneity of the CBPB polymer blends (CBPB-100, CBPB-90, CBPB-50, and CBPB-0). Samples were initially scanned from room temperature to 150° C. under nitrogen at a heating rate of 10° C. per min., followed by cooling at a rate of −40° C. per min. until a temperature of −75° C. was achieved. Samples were then scanned again from −75° C. to 150° C. at a heating rate of 10° C. per min. The glass transition temperature ($T_g$) was determined from the middle of the recorded step change in heat capacity from the second heating run. To determine the miscibility of the two polymers or oligomers in a CBPB blend, the glass transition temperature of the blend was expressed by Equation (2) (the Fox Equation):

$$1/T_g = W_1/T_{g,1} + W_2/T_{g,2} \qquad (2),$$

where $W_i$ is the weight fraction of component i and temperatures are in Kelvin. Results are shown in FIG. 2. FIG. 2 illustrates DSC thermograms of various CBPB blends. Values are reported as the mean±one standard deviation, with n=6. The CBPB blends exhibited a single glass transition temperature that increased with increasing CUPE content under the same polymerization conditions (5 days, 80° C.). The $T_g$ values for CBPB-90 and CBPB-50, based on the $T_g$ values of the individual components CBPB-100 and CBPB-0, were calculated to be 0.41° C. and −9.13° C., respectively.

Figure 3A:
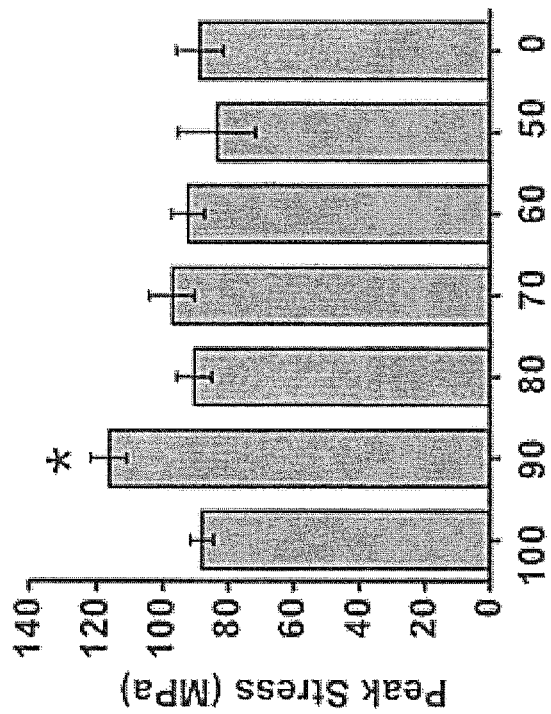
FIG. 3A illustrates the compressive modulus of a series of compositions according to some embodiments described herein.
Figure 3B:
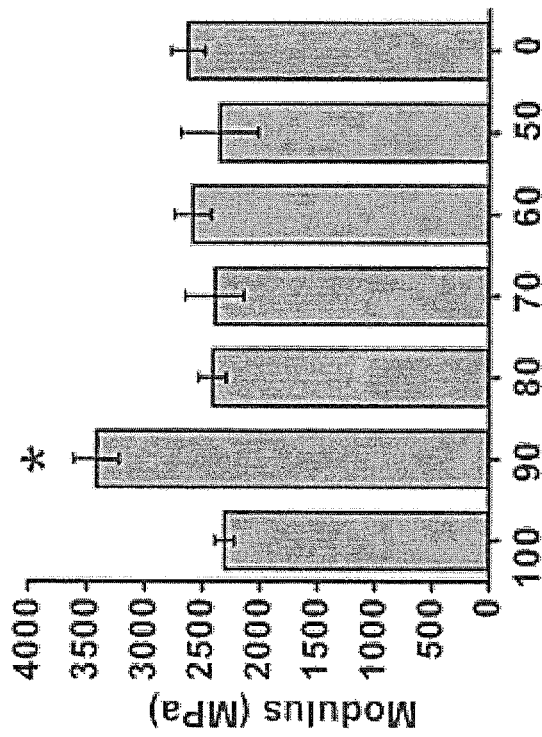
FIG. 3B illustrates the compressive peak strength of a series of compositions according to some embodiments described herein.

Unconfined compression tests were performed on the CBPBHA composites using an Electromechanical Universal testing machine Q Test-150 (MTS, Eden Prairie, Minn., USA). Briefly, cylindrical shaped specimens 6 mm×9 mm (diameter×height) were compressed at a rate of 2 mm per min. to failure. The initial modulus was calculated by measuring the gradient at 10% of compression of the stress-strain curve. Results are shown in Table III and in FIGS. 3A and 3B. FIG. 3A illustrates the compressive modulus of CBPBHA composites. FIG. 3B illustrates the compressive peak strength of CBPBHA composites. The x-axis values represent the CUPE percentage in the CBPB blends.

TABLE III

Mechanical Properties.

| Composition | Compressive Modulus (MPa) | Peak Load (N) | Peak Stress (MPa) |
|---|---|---|---|
| CBPBHA-100 | 2308.17 ± 84.31 | 2308.71 ± 104.47 | 87.93 ± 3.54 |
| CBPBHA-90 | 3419.29 ± 191.97 | 3077.86 ± 159.98 | 116.23 ± 5.37 |
| CBPBHA-80 | 2415.29 ± 118.62 | 2476.86 ± 143.34 | 90.29 ± 5.41 |
| CBPBHA-70 | 2396.14 ± 255.29 | 2694 ± 167.93 | 97.13 ± 6.98 |
| CBPBHA-60 | 2584.43 ± 163.11 | 2530.14 ± 139.43 | 92.30 ± 5.15 |
| CBPBHA-50 | 2352.43 ± 335.83 | 2334 ± 238.75 | 83.47 ± 11.81 |
| CBPBHA-0 | 2628.43 ± 148.14 | 2353.14 ± 156.57 | 88.63 ± 7.17 |

The in vitro degradation rate of disk samples (6 mm diameter×2 mm thick) of the CBPBHA composites was assessed by weight loss over time. The samples were disposed in phosphate-buffered saline (PBS) (pH 7.4) at 37° C. for up to 24 weeks under static conditions. PBS was changed every week to ensure that the pH did not drop below 7. Prior to weighing, samples were extensively rinsed with deionized (DI) water and lyophilized. Weight loss was calculated by comparing the initial weight ($W_0$) with the weight measured at 1, 2, 4, 8, 12, and 24 weeks ($W_t$), as shown in Equation (1):

$$\text{Weight Loss} = (W_0 - W_t)/W_0 \times 100\% \quad (1).$$

Figure 4:
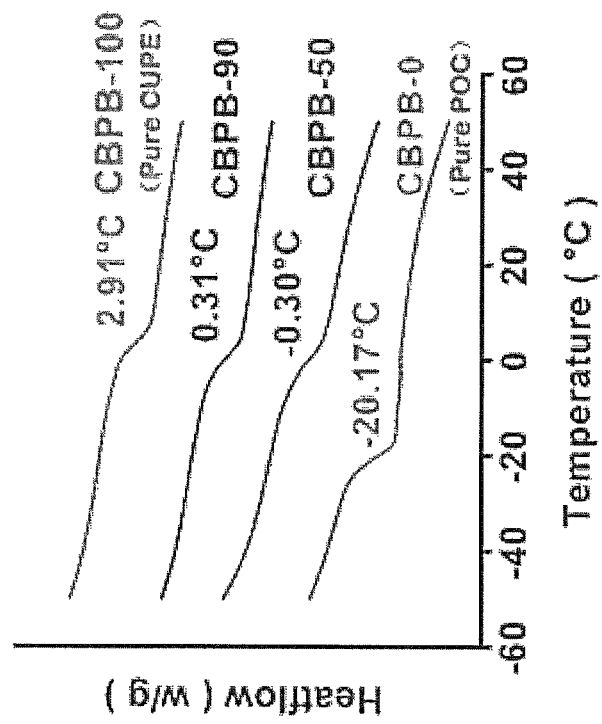
FIG. 4 illustrates the in vitro degradation rate of a series of compositions according to some embodiments described herein.

Results are shown in FIG. 4 as mean±one standard deviation (n=6).

Figure 5:
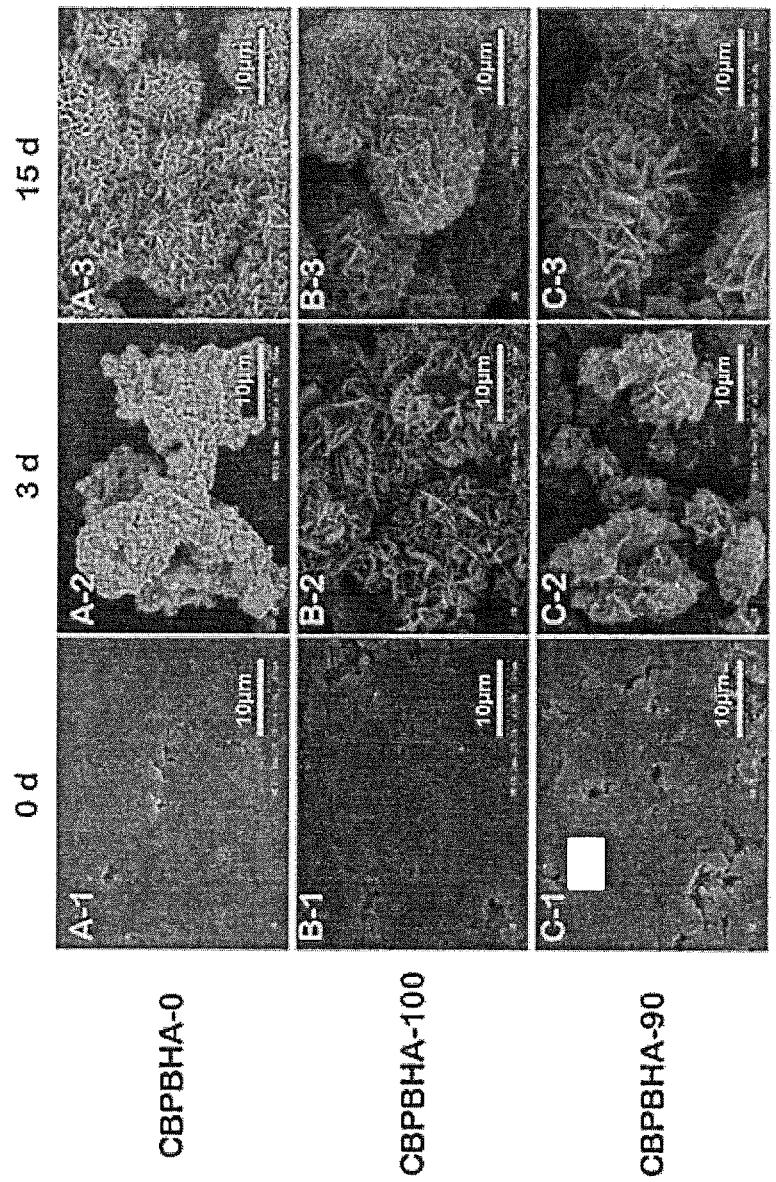
FIG. 5 illustrates scanning electron microscopy (SEM) images of the mineralization of a series of composites according to some embodiments of methods described herein.

In vitro mineralization of CBPBHA composites was assessed using 4× modified simulated body fluid (SBF) solution consisting of (mmol): $Na^+$ (142.0), $K^+$ (5.0), $Mg^{2+}$ (1.5), $Ca^{2+}$ (2.5), $Cl^-$ (103), $HCO_3^-$ (10.0), $HPO_4^{2-}$ (1.0) and $SO_4^{2-}$ (0.5) with the pH adjusted to 7.0 using 1.0 M NaOH for accelerated results. Briefly, composite disks (6 mm diameter×2 mm height) were immersed in 10 mL of the SBF at 37° C. for up to 15 days. SBF was refreshed every other day to maintain the ionic concentration and pH during mineralization. After incubation for various periods of times, the specimens were washed carefully with DI water to remove any soluble inorganic ions and dried in air. Samples were then coated with silver and observed under a scanning electron microscope (SEM) (Hitachi, Pleasanton, Calif., USA). The stoichiometric Ca/P molar ratio was analyzed by energy-dispersive x-ray (EDX) analysis and determined to be 1.39±0.25. As illustrated in FIG. 5, all of the CBPBHA composites induced rapid mineralization. The images labeled A-1, A-2, and A-3 in FIG. 5 correspond to CBPBHA-0 at 0, 3, and 15 days, respectively. A similar labeling scheme is used for the other composites in FIG. 5.

EXAMPLE 3

Methods of Promoting Bone Growth

Methods of promoting bone growth according to some embodiments described herein were carried out as follows. Bone marrow stromal cells (BMSCs) derived from 6 week old male Sprague-Dawley rats were cultured in growth medium containing Minimum Essential Medium Alpha (αMEM) supplemented with 10% (V/V) fetal bovine serum (FBS), 0.25 μg/mL Fungizone, and 1% (V/V) penicillin and streptomycin in 6-well plates at a density of $2 \times 10^5$ cells/well (Day 0). On Day 3 the growth medium was changed into an osteogenic medium consisting of αMEM supplemented with 10% fetal bovine serum, $10^{-7}$ M dexamethasone, 50 μg/mL ascorbic acid (Sigma), 5 mM β-glycerol phosphate (Sigma), 0.25 μg/mL Fungizone, 1% penicillin and streptomycin, and various concentrations of citric acid (0 μM, 2 μM, 20 μM, 200 μM, 1 mM, and 5 mM). After 12 days of osteogenic induction, the BMSCs cultures were stained with Von Kossa staining and imaged by optical microscopy. The numbers of calcium nodules per well were counted in the inverted microscope. The total area of the calcium nodules was also calculated. Results are shown in FIGS. 6A-6C. FIG. 6A illustrates microscope images of Von Kossa staining FIG. 6B illustrates the number of observed calcium nodules. FIG. 6C illustrates the total area of the calcium nodules. It was found that all citrate-supplemented culture media promoted calcium module formation in a dose-dependent manner. A citrate concentration of 20 μM induced the highest number of calcium nodules (black in FIG. 6A) with larger sizes, while the control medium did not facilitate visible calcium nodule formation.

EXAMPLE 4

Methods of Promoting Bone Growth

Figure 7:
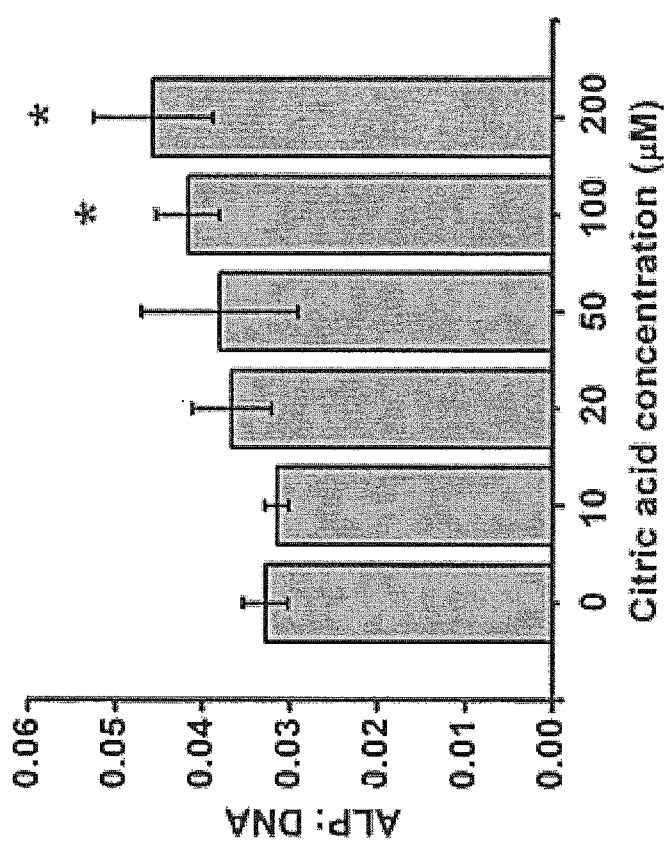
FIG. 7 illustrates the expression of alkaline phosphatase (ALP) according to some embodiments of methods described herein.

Methods of promoting bone growth according to some embodiments described herein were carried out as follows. MG-63 cells (ATCC, Manassas, Va., USA) were cultured in EMEM (Life Technologies, Carlsbad, Calif., USA) supplemented with 10% FBS and 1% penicillin and streptomycin. The MG-63 cells were seeded at 50% confluence in 6-well plates and cultured with EMEM containing different concentrations of citric acid (0 μM, 10 μM, 20 μM, 50 μM, 100 μM, and 200 μM). At 4 days, the cells were lysed and assayed for the presence of alkaline phosphatase (ALP) using an ALP substrate kit (Bio-Rad, Hercules, Calif., USA). The ALP levels were normalized to the total amount of DNA present in the samples as determined by picogreen assay (Life Technologies, Carlsbad, Calif., USA). Results are shown in FIG. 7.

Figure 8A:
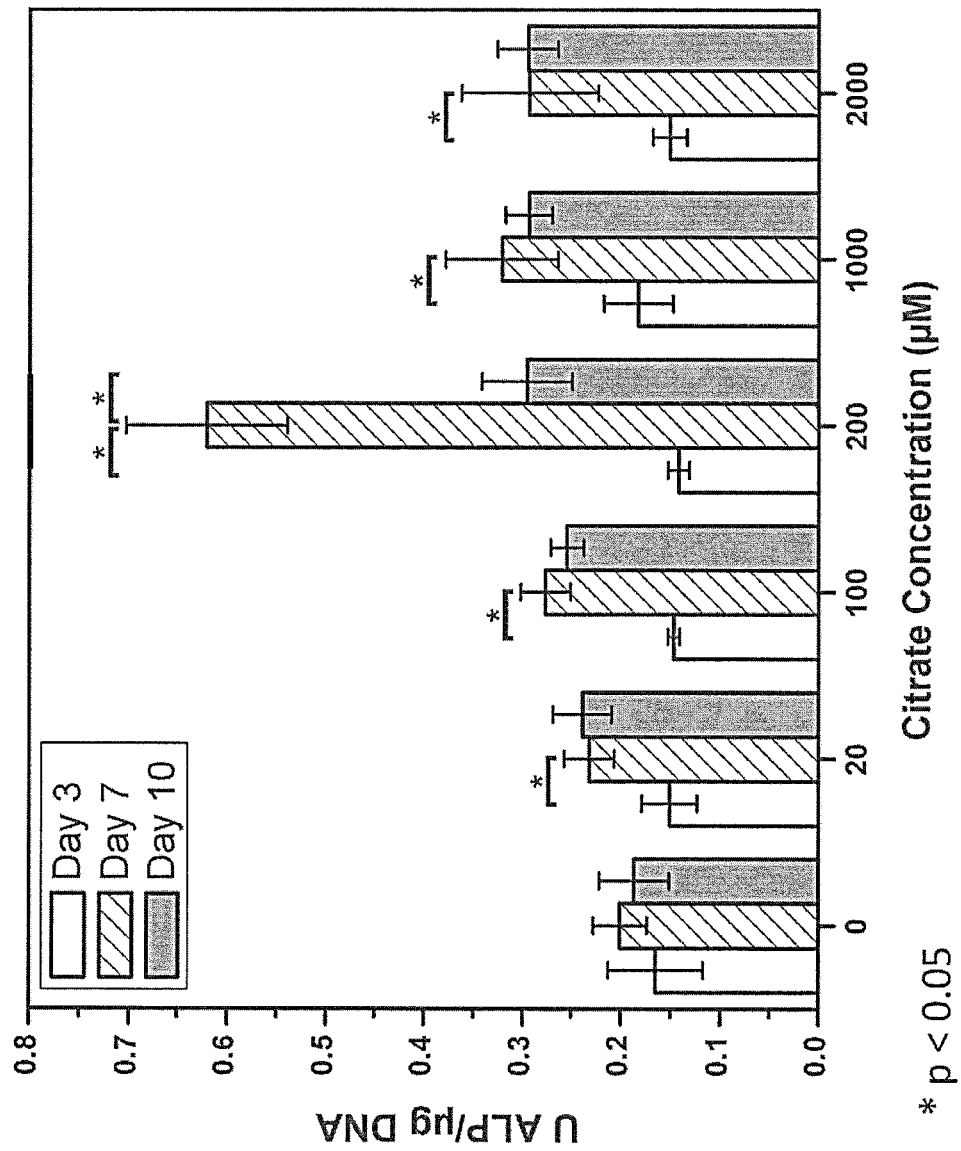
FIG. 8A illustrates the expression ALP according to some embodiments of methods described herein.
Figure 8B:
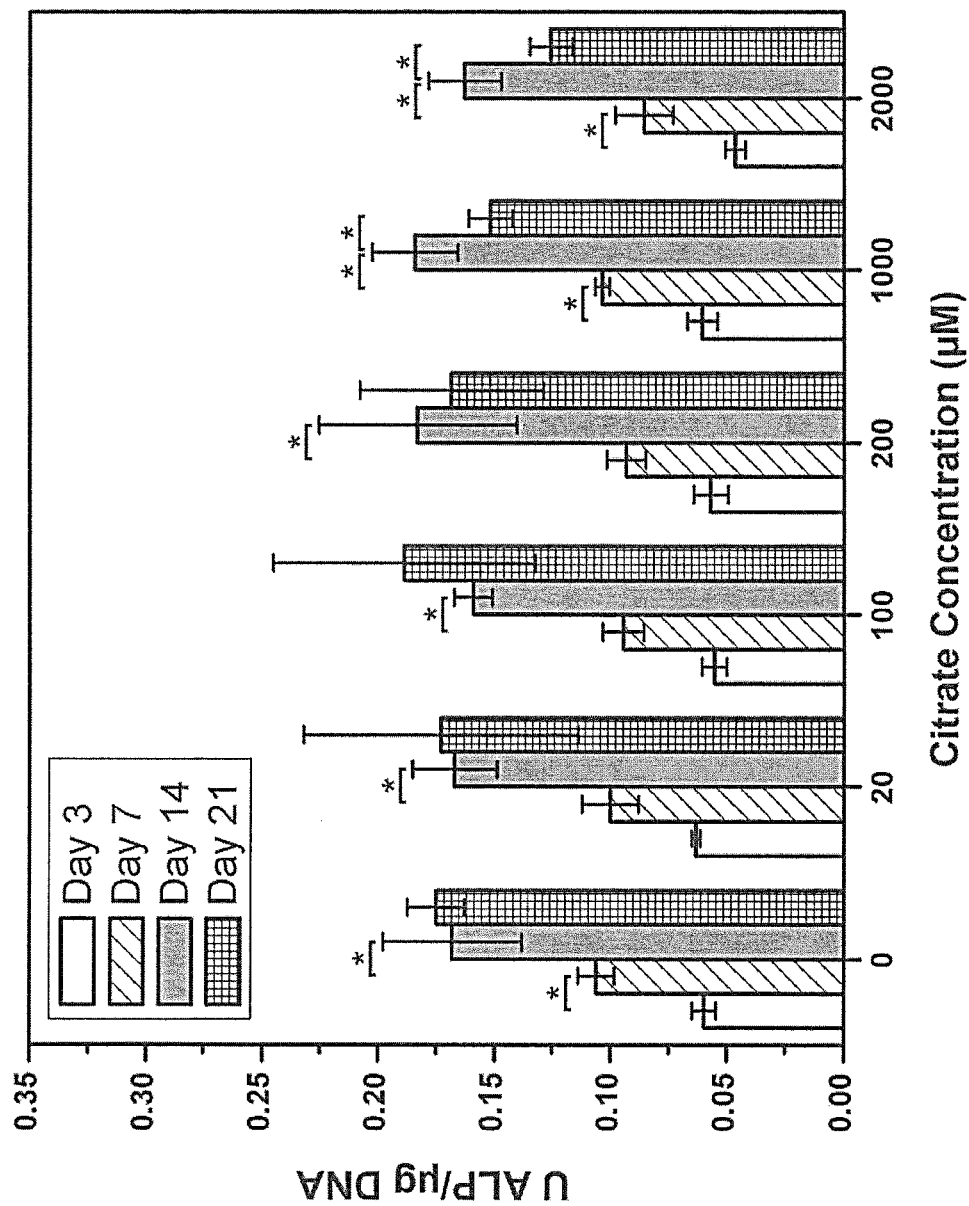
FIG. 8B illustrates the expression of ALP according to some embodiments of methods described herein.

In other experiments, MG-63 cells or MSC cells were cultured and seeded as described above with culture media containing 0 μM, 20 μM, 100 μM, 200 μM, 1000 μM, or 2000 μM citric acid. The cells were assayed for the presence of ALP at various time points, such as Day 3, Day 7, Day 10, Day 14, and Day 21. Results are shown in FIGS. 8A and 8B.

EXAMPLE 5

Methods of Promoting Bone Growth

Figure 9:
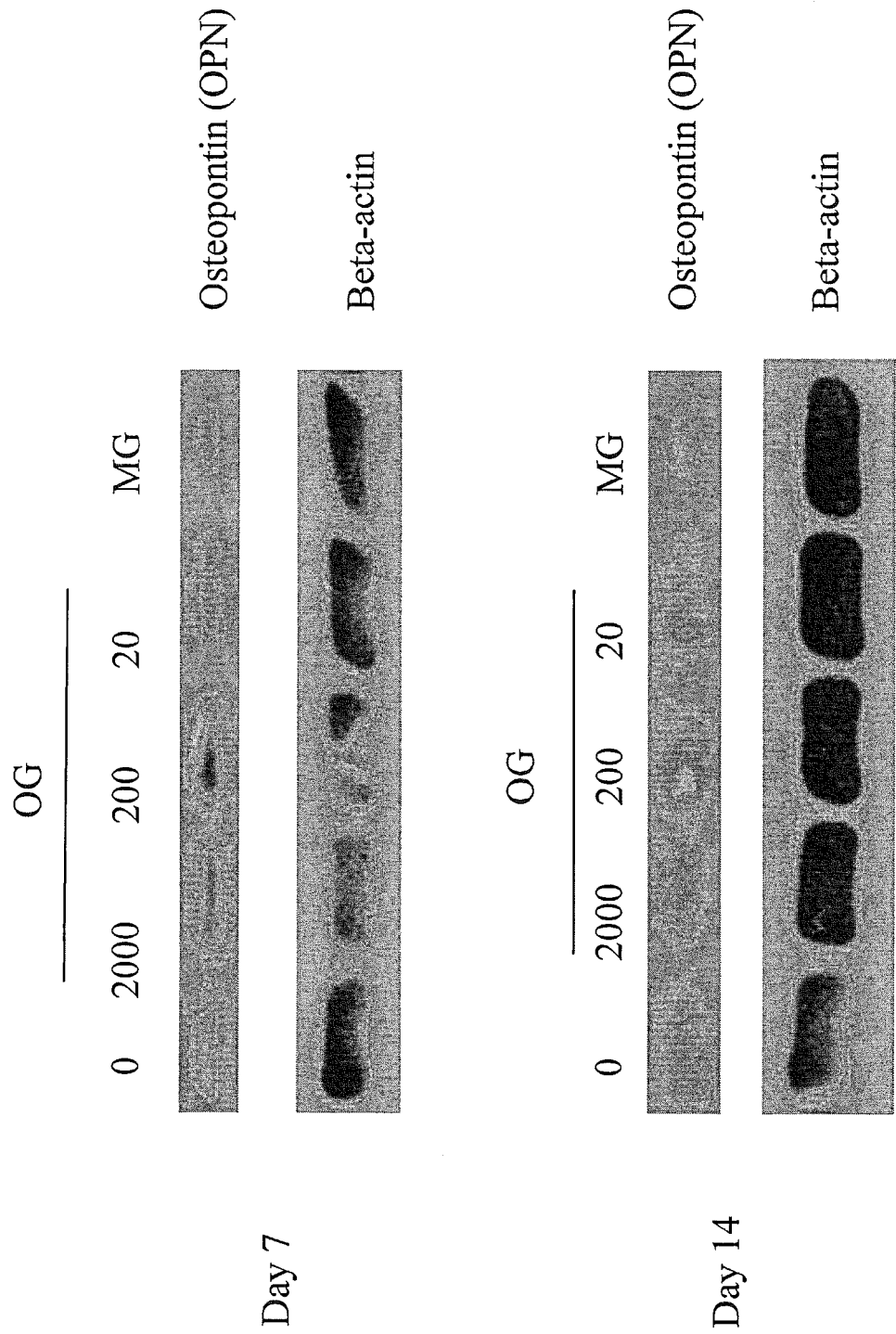
FIG. 9 illustrates osteopontin (OPN) expression according to some embodiments of methods described herein.

Methods of promoting bone growth according to some embodiments described herein were carried out as follows. Human mesenchymal stem cells (hMSCs) (Lonza Walkersville Inc., USA) were cultured in Dulbecco's Modified Eagle's Medium (DMEM) supplemented with 10% FBS and 1% penicillin and streptomycin. For differentiation, hMSCs were switched to an osteogenic medium (OGM) comprising the previous DMEM-based medium further supplemented with $10^{-7}$ M β-glycerophosphate and 50 µM ascorbic acid-2-phosphate. The hMSC cells were seeded at a density of $10^4$ cells/mL after 80-90% confluence in 96-well plates. After adjusting the pH to 7.4, calculated volumes of citrate in the form of citric acid were added to the growth medium to obtain a final citrate concentration of 20 µM, 200 µM, or 2000 µM in the growth medium. The hMSCs were incubated with the citrate-supplemented media at 37° C. with 5% $CO_2$. Media were changed every other day. At pre-determined time points (7 days and 14 days post-addition of citrate), the osteopontin (OPN) protein levels were determined and compared by Western Blot assay following the manufacturer's protocol (Bio-rad Laboratory, USA). Results are shown in FIG. 9. As illustrated in FIG. 9, citrate and OPN expression were closely associated in a dose-dependent relationship.

EXAMPLE 6

Methods of Promoting Bone Growth

Figure 10:
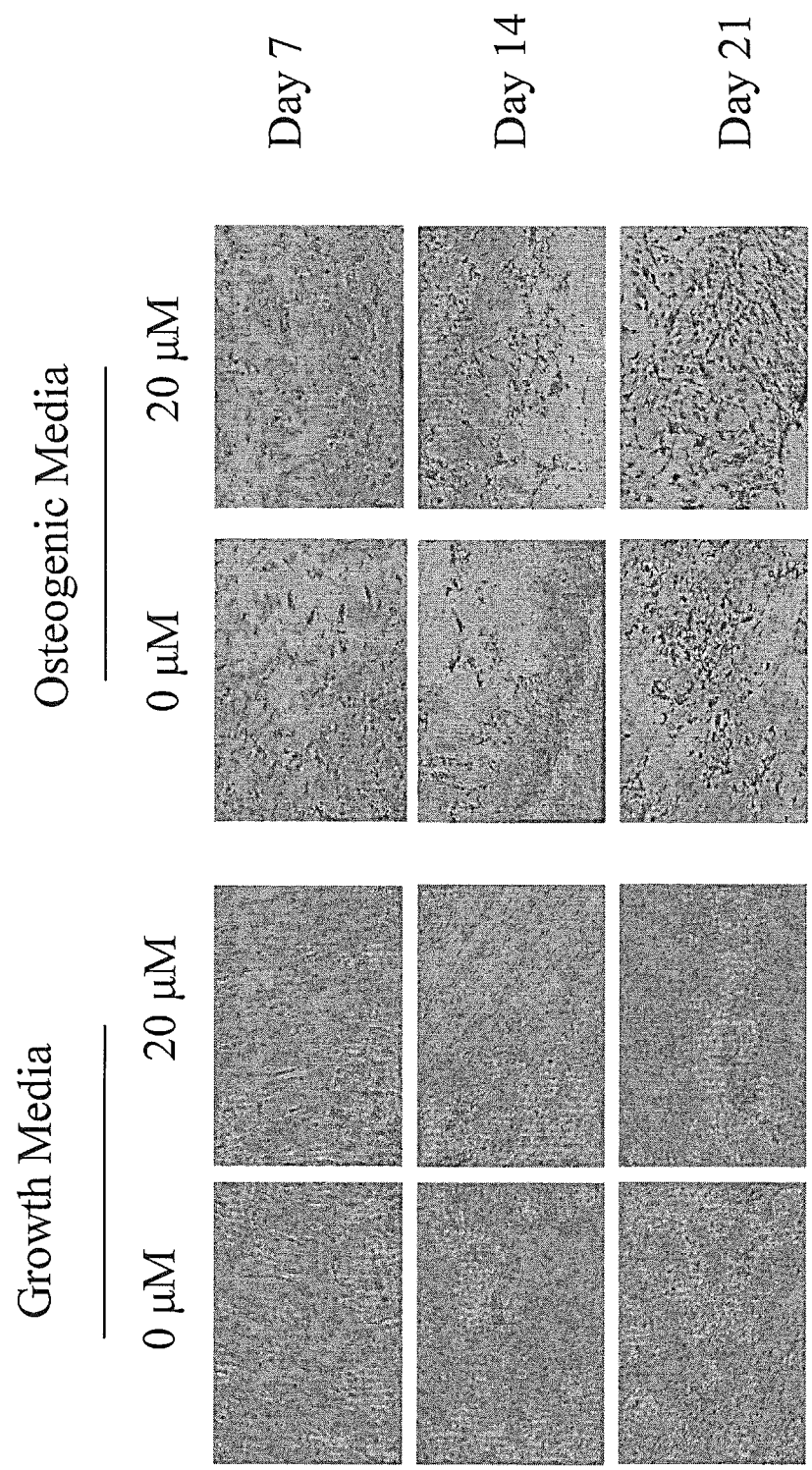
FIG. 10 illustrates optical microscope images of the results of a method of promoting bone growth according to some embodiments described herein.

Methods of promoting bone growth according to some embodiments described herein were carried out as follows. Human mesenchymal stem cells (hMSCs) (Lonza Walkersville Inc., USA) were cultured in Dulbecco's Modified Eagle's Medium (DMEM) supplemented with 10% FBS and 1% penicillin and streptomycin. For differentiation, hMSCs were switched to an osteogenic medium (OGM) comprising the previous DMEM-based medium further supplemented with $10^{-7}$ M dexamethasone, $10^{-2}$ M β-glycerophosphate, and 50 µM ascorbic acid-2-phosphate. The hMSC cells were seeded at a density of $10^4$ cells/mL after 80-90% confluence in 96-well plates. After adjusting the pH to 7.4, calculated volumes of citrate in the form of citric acid were added to the growth medium to obtain a final citrate concentration of 20 µM in the growth medium. The hMSCs were incubated with the citrate-supplemented medium at 37° C. with 5% $CO_2$. Media were changed every other day. At pre-determined time points (7 days, 14 days, and 21 days post-addition of citrate), the cultures were stained by Von Kossa staining and then examined by optical microscope to detect the formation of calcium deposits. Results are shown in FIG. 10. As illustrated in FIG. 10, the exogenous citrate supplement was able to promote calcium deposit formation in differentiated hMSC cultures.

EXAMPLE 7

Methods of Promoting Bone Growth

Methods of promoting bone growth according to some embodiments described herein were carried out as follows. C2C12 cells (ATCC, Manassas, Va., USA) were cultured on CBPB-100, CBPBHA-100, CBPBHA-90, and control glass in 24-well plates in high glucose Dulbecco's modified Eagle's medium (GIBCO, Grand Island, N.Y., USA) supplemented with 10% fetal bovine serum, 100 units/mL penicillin, and 100 µg/mL streptomycin at 95% air and 5% $CO_2$. The total RNA from C2C12 cells was purified using a RNeasy Mini Kit (QIAGEN, Valencia, Calif., USA). RNA was subjected to quantitative real-time RT-PCR, using a TaqMan One-Step RT-PCR Master Mix reagent (Applied Biosystem, Foster City, Calif., USA). Relative transcript levels were analyzed by an ABI 7500 real-time PCR system (Applied Biosystem, Foster City, Calif., USA). Transcript levels were normalized to glyceraldehyde-3-phosphate dehydrogenase (GAPDH) levels. All experiments were done in duplicates and repeated three times. Osteoblast differentiation from C2C12 cells was induced by treatment with BMP-2 (R&D, Minneapolis, Minn., USA). After reaching 60-80% confluency, cells were treated with 300 ng/mL of BMP-2 for 0, 6, 12, 36, and 48 hours. Osterix (OSX) and alkaline phosphatase (ALP) gene expression levels were analyzed as previously described. The morphologies of the C2C12 cells were visualized using scanning electron microscopy. Results are shown in FIGS. 11A-C.

Figure 11A:
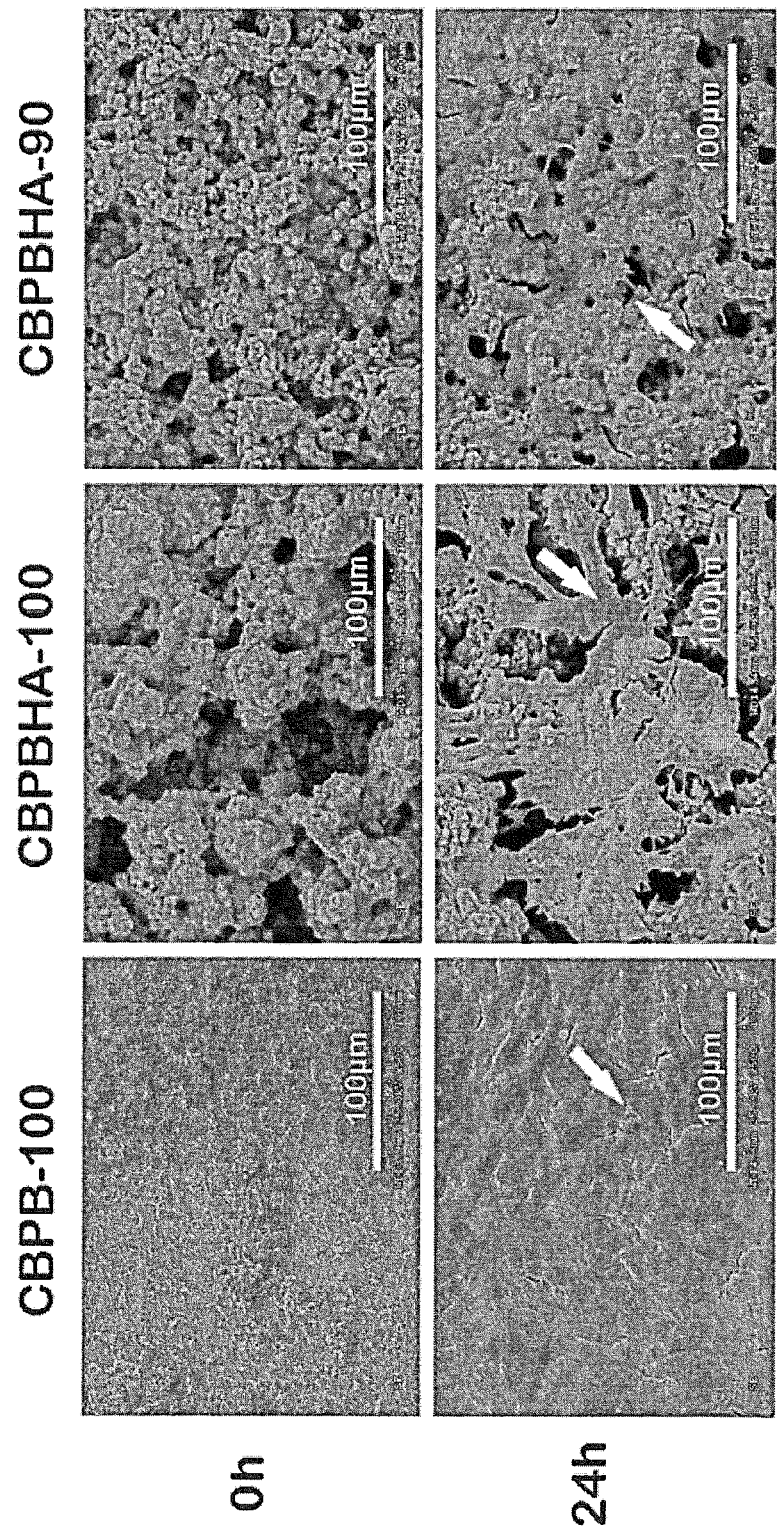
FIG. 11A illustrates SEM images of the results of a method of promoting bone growth according to some embodiments described herein.
Figures 11B, 11C:
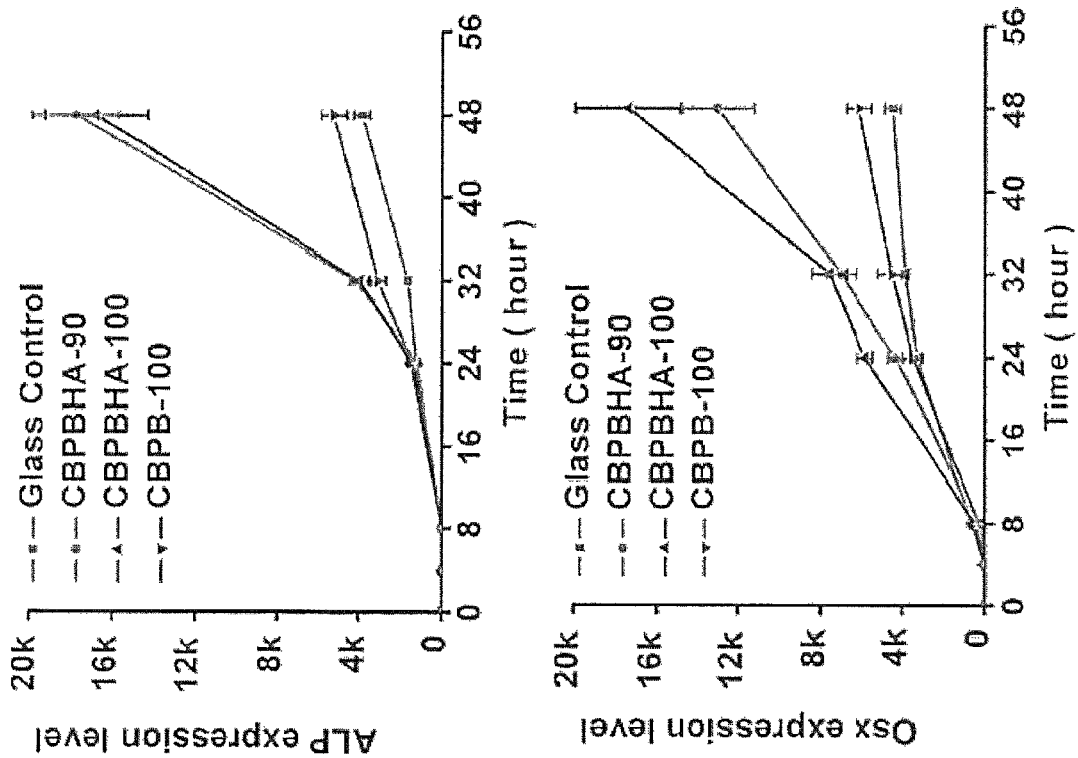
FIG. 11B illustrates the expression of ALP according to some embodiments of methods described herein.
FIG. 11C illustrates the expression of osterix (OSX) according to some embodiments of methods described herein.

After 24 hours, cells formed a monolayer on all CBPBHA composites investigated (FIG. 11A). In addition, ALP and OSX gene expression levels on CBPB-100 increased by 35% and 37%, respectively, compared to a bare glass control after 48 hours of culture. With incorporation of HA to CBPB blends, the ALP and OSX gene expression levels further increased. ALP and OSX gene expression on the plates coated with CBPBHA-90 composite increased by 362% and 191%, respectively, and the expression levels on the plates coated with CBPBHA-100 increased by 336% and 290%, respectively, compared to a bare glass control after 48 hours of culture. When compared to CBPB-100 coated plates after 48 hours, ALP and OSX expression on CBPBHA-90 composites increased by 243% and 113%, respectively, while ALP and OSX expression on CBPBHA-100 composites increased by 224% and 185%, respectively (FIGS. 11B and 11C).

EXAMPLE 8

Methods of Promoting Bone Growth

Figure 12B:
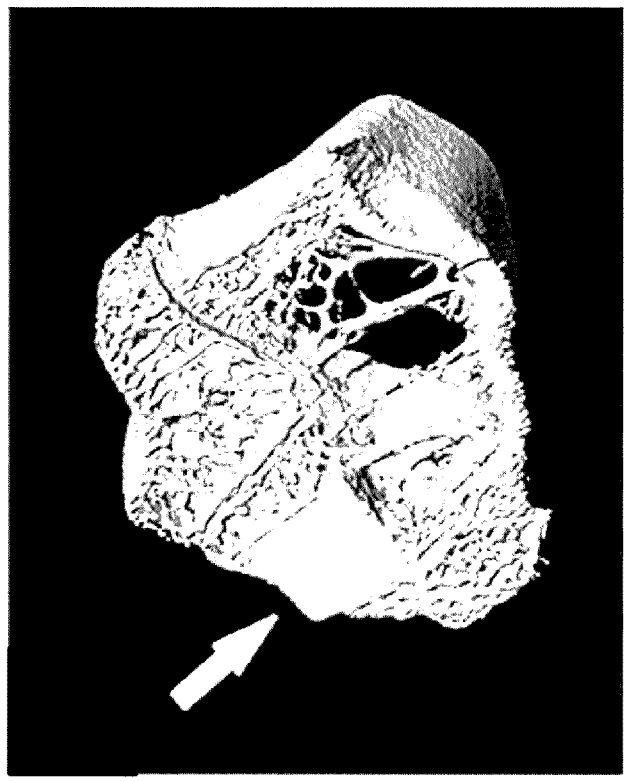
FIG. 12B illustrates a micro-CT image of the results of a method of promoting bone growth according to one embodiment described herein.
Figure 12A:
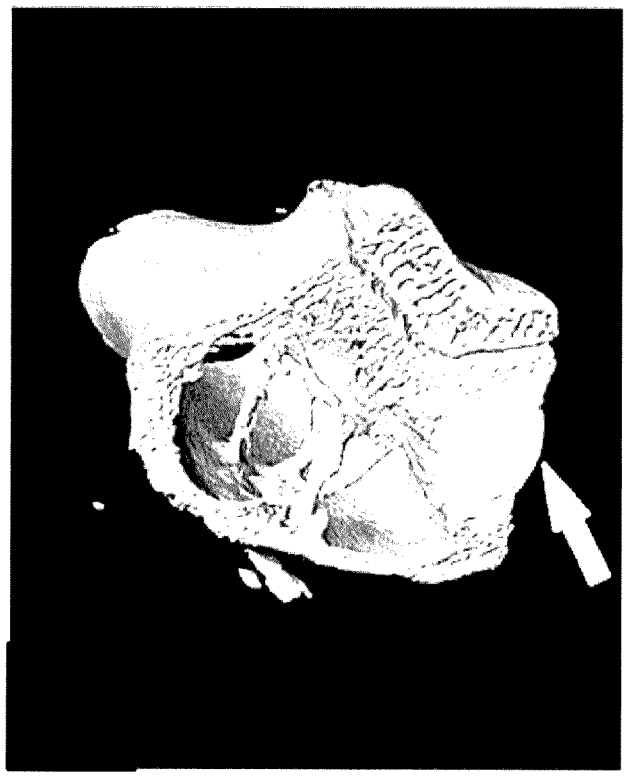
FIG. 12A illustrates a micro-CT image of the results of a method of promoting bone growth according to one embodiment described herein.
Figure 13:
FIG. 13 illustrates two micro-CT images of the results of a method of promoting bone growth according to one embodiment described herein.

Methods of promoting bone growth according to some embodiments described herein were carried out as follows. Twelve New Zealand white rabbits weighing between 2.3 and 2.7 kg were used to assess the biocompatibility and osteointegration properties of CBPBHA-100 and CBPBHA-90 composites. Cylindrical samples were implanted into the lateral femoral condyles of rabbit knees. After 6 weeks of implantation, micro-CT images showed the complete fusion of implants and surrounding new bone tissues, as seen in FIGS. 12A and 12B. FIG. 12A corresponds to CBPBHA-100, and FIG. 12B corresponds to CBPBHA-90. Additional, newly formed bone was observed in contact with the implant in the bone marrow cavity, where originally there was no bone. Further, there was no evidence of chronic inflammation (fibrocapsule formation) or degenerative changes around the implant. On gross histological examination, the implants appeared well integrated with the surrounding bone. No implant loosening was detected, as shown in toluidine staining and von Kossa staining for surrounding bone tissues. Bone-to-implant contact (BIC) results indicated that the bone-to-implant (osteointegration) was as high as 94.74%, as seen in FIG. 13. FIG. 13 illustrates 2-D micro-CT images of the CBPBHA-90 implants with the surrounding bone of the lateral femoral condyle at 6 weeks post-implantation. In addition, there was no bone resorption observed at the interface of the undecalcified bone. Further, there were no positively stained macrophages found at the interface of implants and surrounding tissues.

All animal experiments were carried out in compliance with a protocol approved by Southern Medical University's Animal Care and Use Committee (Guangzhou, CHINA). The animals were randomly divided into 2 groups, and anesthetized by ketamine (40 mg/kg IM) and xylazine (5-7 mg/kg IM) supplemented with isoflurane (1-2% inhalation). Next, a 1.5 cm medial incision on the lateral knee was created to expose the lateral femoral condyle. Using a mosaicplasty harvester (Smith & Nephew, Memphis, Term., USA), a 4×3 mm (diameter×depth) bone defect was drilled in both the right and left lateral femoral condyles for the CBPBHA-100 and CBPBHA-90 groups, respectively. Implants formed from the CBPBHA-100 and CBPBHA-90 composites and matching the dimensions of the defect were inserted according to the grouping via press fit. After all surgical procedures, the rabbits were kept in cages and maintained with a regular laboratory diet. The knees were harvested at 6 weeks post-implantation and stored in 10% neutral-buffered formalin. Gross examination was documented with a digital camera. Computer tomography analysis was conducted using a Micro-CT imaging system (ZKKS-MCT-Sharp-III scanner, Caskaisheng, CHINA). The scanning system was set to 70 kV, 30 W, and 429 µA. The volume of interest was defined as bone tissue around the implants, which included the entire trabecular compartment extending 8 mm from the longitudinal axis of the implant. The extent of implant osteointegration is generally reflected by its bone-to-implant contact (BIC) measurement. BIC was calculated as a percentage of the newly formed bone length over the total implant perimeter based on Micro-CT images.

For histological analysis, paraffin-embedded decalcified tissues were cut into 4 µm sections, which were then deparaffinated, hydrated, and stained with hematoxylin-eosin (H&E). For immunohistochemical staining, paraffin-embedded sections were deparaffinated and hydrated through a graded series of alcohol. Endogenous peroxidase activity was blocked with 0.3% hydrogen peroxide in PBS. Then the sections were blocked with bovine serum albumin (1:100 dilution) and incubated with the primary antibody of CD68 and CD163 (Auragene, Changsha, China, 1:50 dilution) at 4° C. overnight. The sections were washed with PBS three times and incubated with secondary anti-mouse IgG for 1 h at 37° C. The colorization was developed in DAB solution and counterstained by hematoxylin. The inflammatory reaction surrounding the implant was assessed by two individual pathologists in a blinded and randomized fashion from H&E stained sections and IHC staining. The source of the positive control group was harvested from the healing tissue of the rat's Achilles tendon 1 week post-tenotomy, which has been featured by inflammatory response. IHC staining was performed for CD163 and CD68 to detect macrophages. The macrophages appeared brown in the cells with hematoxylin stained nuclei.

EXAMPLE 9

Methods of Inhibiting Cancer Growth

Figure 14:
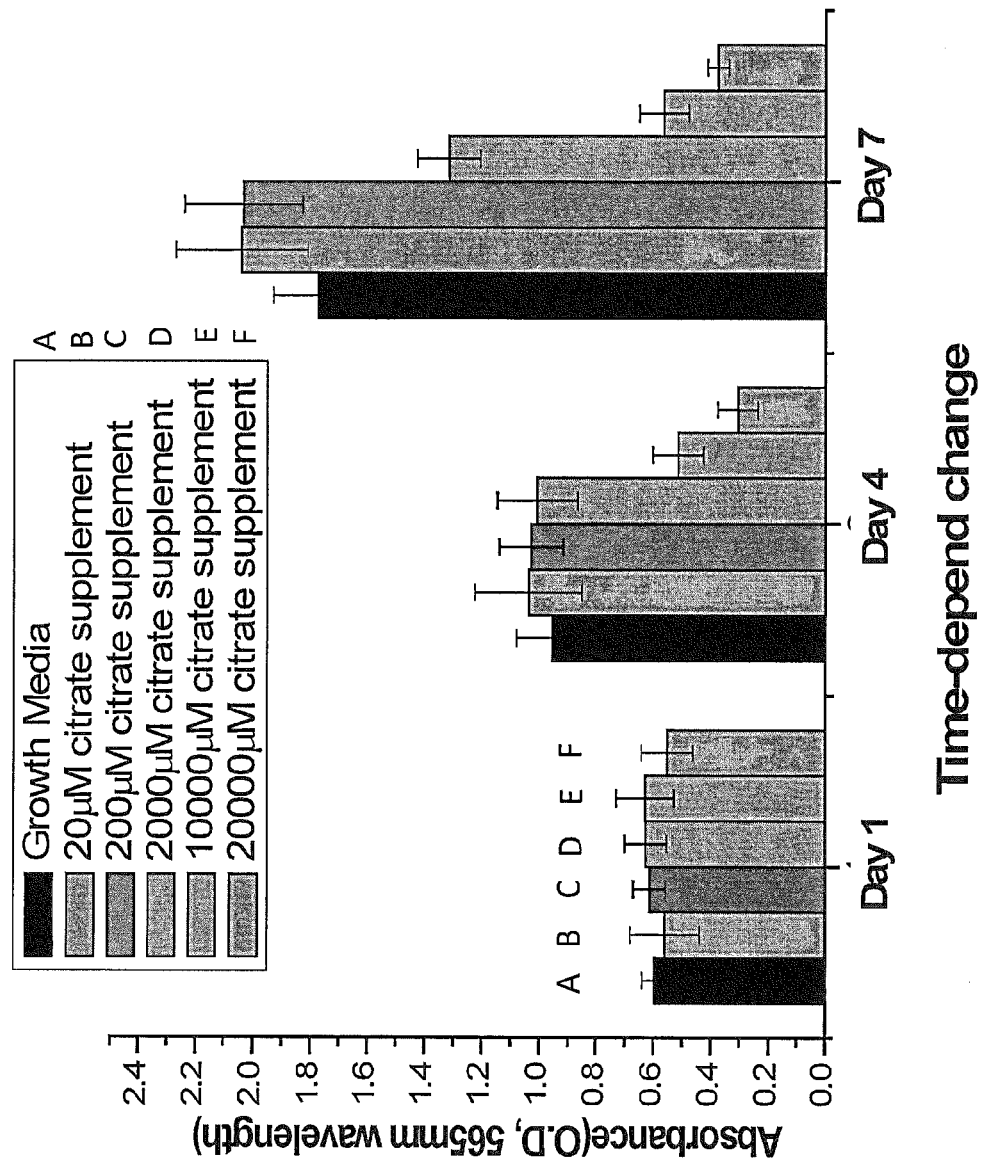
FIG. 14 illustrates cell proliferation data corresponding to one embodiment of a method described herein.
Figure 15:
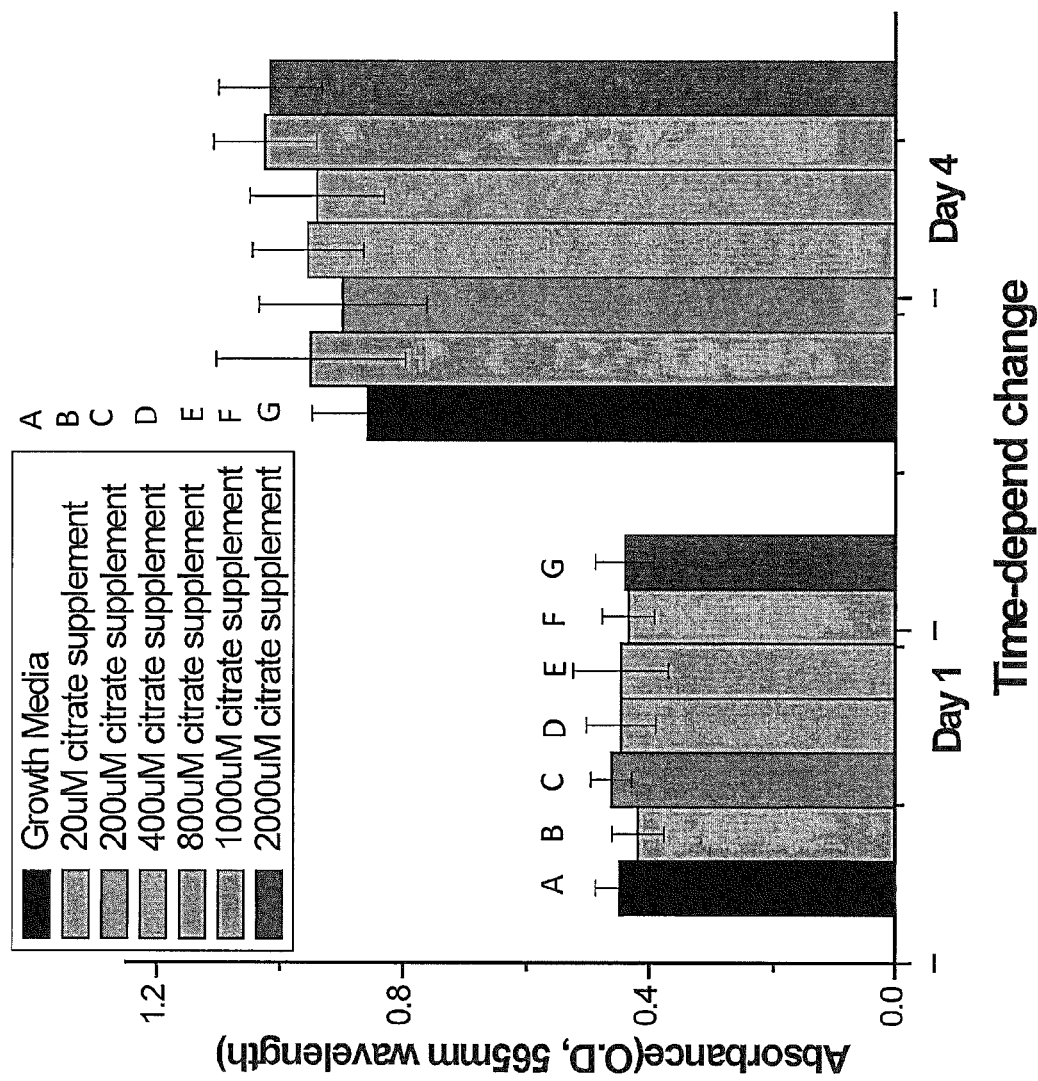
FIG. 15 illustrates cell proliferation data corresponding to one embodiment of a method described herein.

Methods of inhibiting cancer growth according to some embodiments described herein were carried out as follows. First, the effect of citrate on cell proliferation was investigated. Human mesenchymal stem cells (hMSCs) (Lonza Walkersville Inc., USA) were cultured in growth medium composed of Dulbecco's Modified Eagle's Medium (DMEM) supplemented with 10% FBS and 1% penicillin/streptomycin and then seeded in a 96-well plates at a density of $10^4$ cells/mL after 80-90% confluence. After adjusting the pH to 7.4, calculated volumes of citrate in the form of citric acid were added to the growth medium to obtain a final citrate concentration of 20 µM, 200 µM, 400 µM, 800 µM, 1000 µM, 2000 µM, 10,000 µM, or 20,000 µM in the growth medium. The hMSCs were incubated with the citrate-supplemented media at 37° C. with 5% $CO_2$. Media were changed every other day. At pre-determined time points (1 day, 4 days, and 7 days post-addition of citrate), the proliferation of the hMSCs was determined by MTT (methylthiazolyldiphenyl-tetrazolium bromide) assay following the manufacturer's protocol (Sigma, USA). After incubating at 37° C. for 4 hrs in MTT working solution, the hMSCs in the 96-well plates were submerged in dimethylsulfoxide (DMSO) for 15 minutes on an orbital shaker under dark conditions. The 96-well plates were then placed on a Microplate Reader to obtain absorbance values at 595 nm. In addition, live/dead staining was carried out at pre-determined time points (1 day, 4 days, and 7 days). The hMSCs were stained with live/dead working solution (Life Technologies Inc., USA) for 30 minutes and then observed under a Nikon Inverted Fluorescence Microscope to determine cell viability. The results are shown in FIGS. 14 and 15. As indicated in FIGS. 14 and 15, citrate was found not to affect hMSC proliferation in the concentration window of 20-2000 µM but to suppress hMSC proliferation at higher concentrations (above 2000 µM and up to 20,000 µM).

Figure 16:
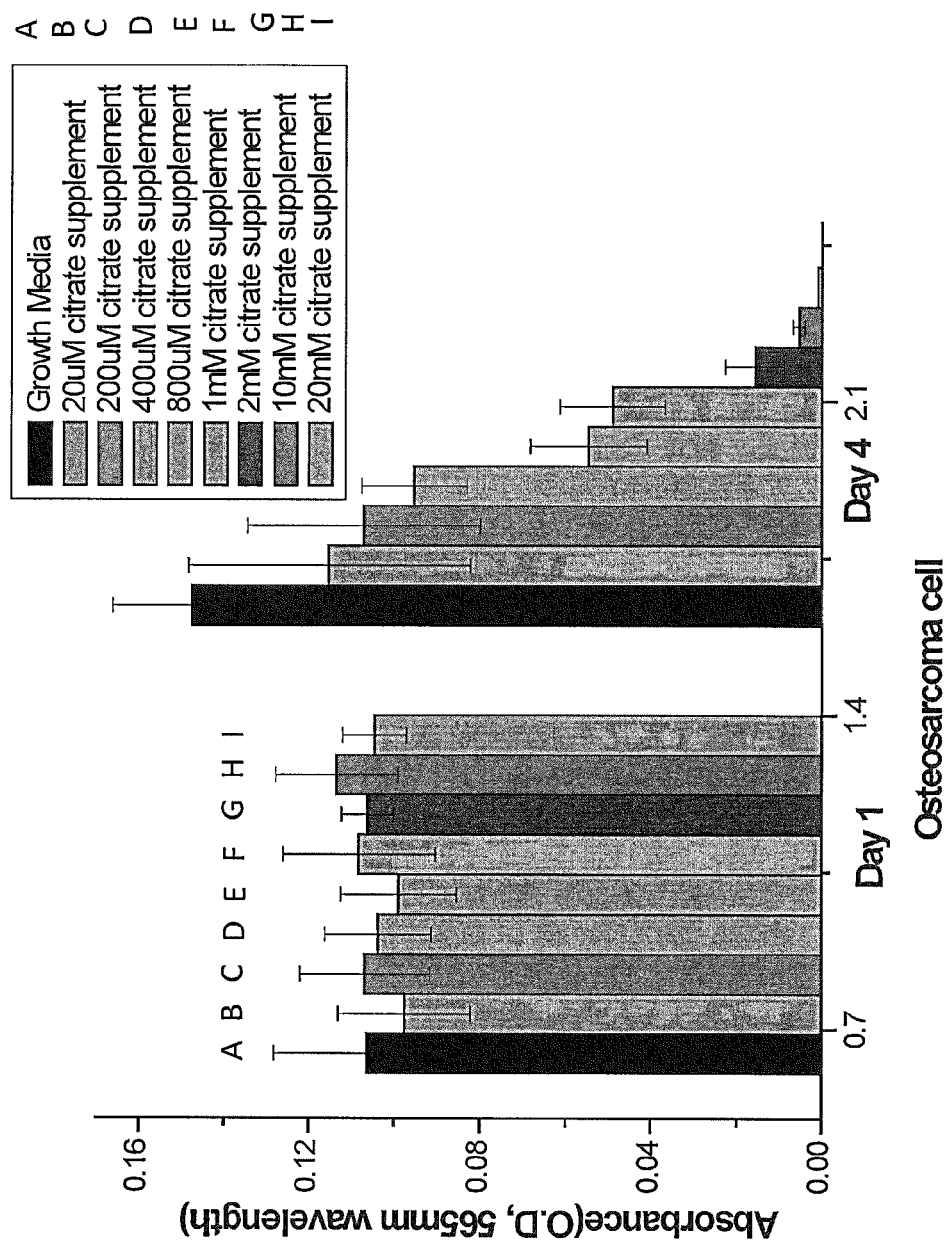
FIG. 16 illustrates cell proliferation data corresponding to one embodiment of a method described herein.

In another experiment, hMSCs and osteosarcoma cells (Saos-2 cells) (ATCC Inc., USA) were cultured in the presence of citrate. The hMSCs were cultured as described above. The Saos-2 cells were cultured in McCoy's 5A medium (Lonza Walkersville Inc., USA) supplemented with 10% FBS and 1% penicillin/streptomycin. Both hMSCs and Saos-2 cells were seeded in 96-well plates at a density of $10^4$ cells/mL after 80-90% confluence. After adjusting the pH to 7.4, calculated volumes of citrate in the form of citric acid were added to the growth media to obtain a final citrate concentration of 20 µM, 200 µM, 400 µM, 800 µM, 1000 µM, 2000 µM, 10,000 µM, or 20,000 µM in the growth media. The hMSCs and the Saos-2 cells were incubated with the citrate-supplemented media at 37° C. with 5% $CO_2$. Media were changed every other day. At pre-determined time points (1 day and 4 days post-addition of citrate), the proliferations of the hMSCs and Saos-2 cells were determined as described above. The results are shown in FIGS. 15 and 16. As indicated in FIGS. 15 and 16, citrate was found to inhibit Saos-2 cell proliferation at concentrations above 800 µM. In addition, at concentrations above 2000 µM, most Saos-2 cells were killed.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of promoting bone growth comprising:
   (1) providing an amount of a first citrate-presenting composition to a population of bone cells at a first stage of cell development selected to obtain a first cell differentiation or phenotype progression; and
   (2) providing an amount of a second citrate-presenting composition to the population of bone cells at a second stage of cell development selected to obtain a second cell differentiation or phenotype progression;
   wherein the amount of second citrate-presenting composition provided in step (2) is in addition to the amount of the first citrate-presenting composition provided in step (1); wherein the first citrate-presenting composition comprises a polymer or oligomer comprising a citrate moiety; and
   wherein both the first and second citrate-presenting compositions are provided to the population of bone cells in the form of an aqueous mixture or solution.

2. The method of claim 1, wherein the first citrate-presenting composition promotes osteoblast phenotype progression in the population of bone cells.

3. The method of claim 1, wherein the bone cells comprise bone stem cells.

4. The method of claim 1, wherein the bone cells are in vitro.

5. The method of claim 1, wherein the first citrate-presenting composition comprises citric acid or aqueous citrate.

6. The method of claim 1 further comprising releasing citrate from the polymer or oligomer by degrading the polymer or oligomer.

7. The method of claim 6, wherein degrading the polymer or oligomer comprises hydrolyzing an ester bond of the polymer or oligomer.

8. The method of claim 1, wherein the first citrate-presenting composition comprises a polymer or oligomer having the structure of Formula (I):

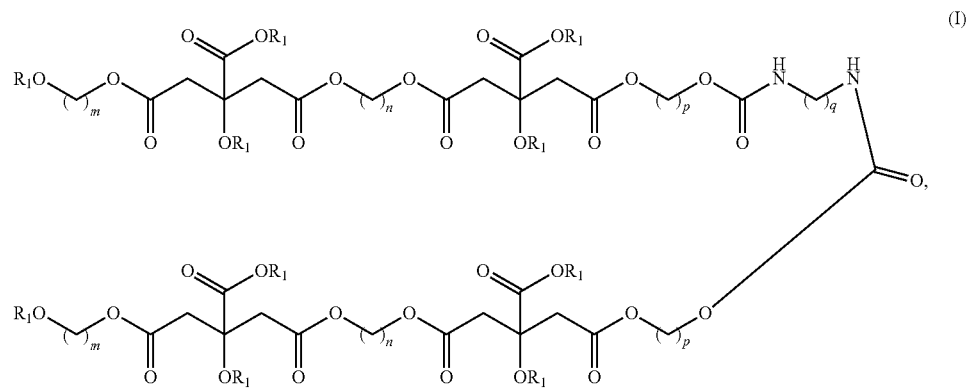

wherein
R$_1$ is —H, —OC(O)NH$\sim\sim\sim$, or $\sim\sim\sim$;
$\sim\sim\sim$ represents an additional chain of repeating units having the structure of Formula (I); and
m, n, and p are 8; and
q is 6.

9. The method of claim 1, wherein the first citrate-presenting composition comprises a polymer or oligomer having the structure of Formula (II):

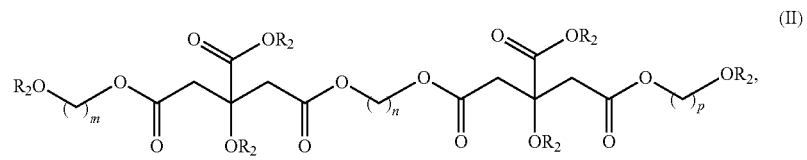

wherein

R$_2$ is —H or ;

 represents an additional chain of repeating units having the structure of Formula (II); and m, n, and p are 8.

10. The method of claim 1, wherein the first citrate-presenting composition comprises:
  a first polymer or oligomer having the structure of Formula (I)

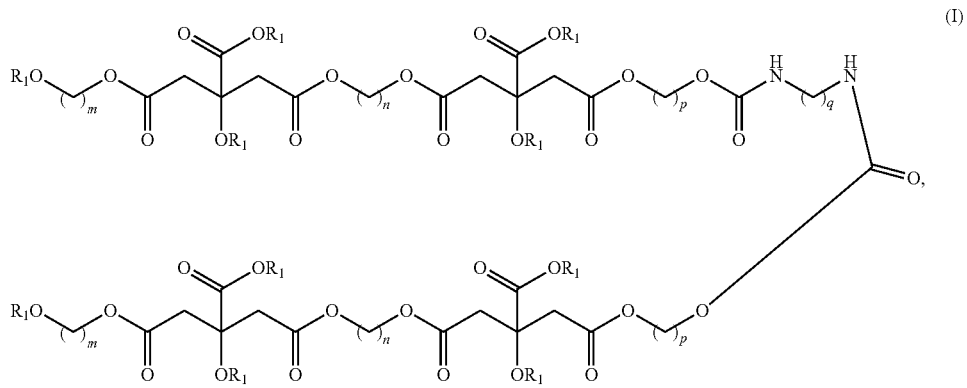

wherein the first polymer or oligomer is blended with the second polymer or oligomer.

11. The method of claim 10, wherein the first polymer or oligomer and the second polymer or oligomer are cross linked with one another to form a polymer network.

12. The method of claim 11 further comprising a particulate material dispersed in the polymer network, the particulate material comprising one or more of hydroxyapatite, tricalcium phosphate, biphasic calcium phosphate, bioglass, ceramic, magnesium powder, magnesium alloy, and decellularized bone tissue particles.

13. The method of claim 1 further comprising providing a biological factor to the bone cells.

14. The method of claim 13, wherein the biological factor comprises BMP-2.

wherein

R$_1$ is —H, —OC(O)NH, or ;

 represents an additional chain of repeating units having the structure of Formula (I); and m, n, and p are 8; and q is 6; and a second polymer or oligomer having the structure of Formula (II):

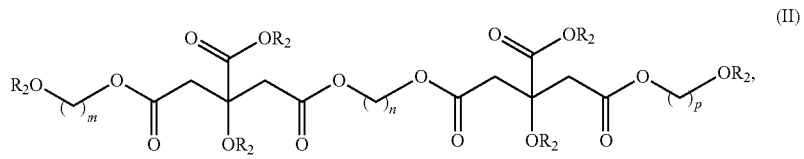

wherein

R$_2$ is —H or ;

 represents an additional chain of repeating units having the structure of Formula (II); and m, n, and p are 8, 15. The method of claim 1, wherein the first citrate-presenting composition and the second citrate-presenting composition have the same composition.

* * * * *